United States Patent
Liang et al.

(10) Patent No.: US 11,071,589 B2
(45) Date of Patent: Jul. 27, 2021

(54) METHOD AND SYSTEM FOR INTERACTIVE LAPAROSCOPIC ULTRASOUND GUIDED ABLATION PLANNING AND SURGICAL PROCEDURE SIMULATION

(71) Applicant: EDDA TECHNOLOGY, INC., Princeton, NJ (US)

(72) Inventors: Cheng-Chung Liang, West Windsor, NJ (US); Li Fan, Belle Mead, NJ (US); Guo-Qing Wei, Plainsboro, NJ (US); Xin Dou, Plainsboro, NJ (US); Jianzhong Qian, Princeton Junction, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 518 days.

(21) Appl. No.: 15/615,630

(22) Filed: Jun. 6, 2017

(65) Prior Publication Data

US 2017/0347988 A1    Dec. 7, 2017

Related U.S. Application Data

(60) Provisional application No. 62/346,189, filed on Jun. 6, 2016.

(51) Int. Cl.
*A61B 34/00* (2016.01)
*A61B 34/10* (2016.01)
(Continued)

(52) U.S. Cl.
CPC ............ *A61B 34/10* (2016.02); *A61B 8/0841* (2013.01); *A61B 17/320068* (2013.01);
(Continued)

(58) Field of Classification Search
CPC .............................. A61B 34/10; A61B 8/0841
See application file for complete search history.

(56) References Cited

U.S. PATENT DOCUMENTS

| 6,413,219 B1 | 7/2002 | Avila et al. |
| 7,171,255 B2 | 1/2007 | Holupka et al. |

(Continued)

FOREIGN PATENT DOCUMENTS

| EP | 2666432 A1 | 11/2013 |
| WO | 2016081321 A2 | 5/2016 |

OTHER PUBLICATIONS

International Search Report and Written Opinion dated Aug. 7, 2017 in International Application PCT/US2017/036184.
(Continued)

*Primary Examiner* — Joseph M Santos Rodriguez
(74) *Attorney, Agent, or Firm* — Pillsbury Winthrop Shaw Pittman LLP

(57) ABSTRACT

Systems and methods relating to placement of an ultrasound transducer for a procedure. In a non-limiting embodiment, a 3D environment including images of a body region of a patient, as well as images including a first virtual representation of an ablation needle at a first location and a second virtual representation of an ultrasound transducer at a second location is rendered on a display device. A determination may be made as to whether the first and second virtual representations collide at a first collision point. If so, at least one parameter associated with an orientation and/or position of the second virtual representation may be adjusted. A determination may then be made as to whether or not the first and second virtual representations still collide and, in response to determining that there is no collision, position data indicating the location of the second virtual representation after the adjustment, is stored.

29 Claims, 21 Drawing Sheets

(51) Int. Cl.
*A61B 8/08* (2006.01)
*A61B 17/32* (2006.01)
*G16H 50/50* (2018.01)
*A61B 17/34* (2006.01)
*G16H 30/20* (2018.01)

(52) U.S. Cl.
CPC ............. *A61B 2017/320069* (2017.08); *A61B 2017/3413* (2013.01); *A61B 2034/101* (2016.02); *A61B 2034/102* (2016.02); *A61B 2034/105* (2016.02); *A61B 2034/107* (2016.02); *G16H 30/20* (2018.01); *G16H 50/50* (2018.01)

(56) References Cited

U.S. PATENT DOCUMENTS

| | | |
|---|---|---|
| 7,488,289 B2 | 2/2009 | Suorsa et al. |
| 8,038,618 B2 | 10/2011 | Thiele et al. |
| 8,585,598 B2 | 11/2013 | Razzaque et al. |
| 8,852,111 B2 | 10/2014 | Park et al. |
| 9,101,397 B2 | 8/2015 | Guthart et al. |
| 9,107,698 B2 | 8/2015 | Razzaque et al. |
| 9,155,518 B2 | 10/2015 | Yamagata |
| 9,251,721 B2 * | 2/2016 | Lampotang ........... G09B 23/285 |
| 10,307,079 B2 * | 6/2019 | Wei ........................ A61B 5/066 |
| 2006/0073454 A1 * | 4/2006 | Hyltander ............ G09B 23/285 |
| | | 434/262 |
| 2006/0093089 A1 * | 5/2006 | Vertatschitsch ...... A61N 5/1049 |
| | | 378/65 |
| 2007/0021738 A1 | 1/2007 | Hasser et al. |
| 2012/0289830 A1 | 11/2012 | Halmann et al. |
| 2014/0078138 A1 | 3/2014 | Martin et al. |
| 2014/0142426 A1 * | 5/2014 | Razzaque ........... A61B 18/1477 |
| | | 600/424 |
| 2015/0005785 A1 * | 1/2015 | Olson .................... A61B 34/37 |
| | | 606/130 |
| 2015/0056591 A1 | 2/2015 | Tepper et al. |

OTHER PUBLICATIONS

International Preliminary Report on Patentability dated Dec. 20, 2018 in International Application PCT/US2017/036184.
Extended European Search Report dated Jan. 15, 2020 in European Application 17810872.6.
Office Action dated Jan. 5, 2021, in Chinese Application 201780034979.6

* cited by examiner

METHOD AND SYSTEM FOR INTERACTIVE LAPAROSCOPIC ULTRASOUND GUIDED ABLATION PLANNING AND SURGICAL PROCEDURE SIMULATION

CROSS REFERENCE TO RELATED APPLICATIONS

This application claims the priority benefit of U.S. Provisional Patent Application No. 62/346,189, which was filed on Jun. 6, 2016, and the disclosure of which is incorporated herein by reference in its entirety.

BACKGROUND OF THE INVENTION

1. Field of the Invention

This invention is generally related to interactive laparoscopic ultrasound guided ablation procedure planning.

2. Description of Related Art

Laparoscopic ultrasound guided ablation ("LUSA") is a type of minimally invasive surgical procedures to treat some unresectable cancer lesions. Usually, this procedure requires a surgeon to make one small incision for an ablation needle and one small incision for an ultrasound probe. The surgeon then operates the ultrasound probe to track the ablation needle's location while advancing the ablation needle towards a target area. An ultrasound transducer head is then placed on a surface of a vital organ, such as, for example, a liver, which contains one or more lesions to be treated. The location and orientation of the ultrasound transducer head can be adjusted through controls located on the ultrasound probe, as well as by micro-moving the probe itself.

It is difficult, however, to determine how to accurately place and maneuver a laparoscopic ultrasound probe and an ablation needle at the same time so that the ablation needle's tip can always be seen in laparoscopic ultrasound images captured by the ultrasound probe during the procedure. It is even more challenging to perform such a task when not being able to physically see the surgical instruments, the target, and any vital organs directly since they are located inside the abdominal cavity.

Computer simulation can help physicians in preparing for the actual maneuvers that may need to be performed during surgery similar to an airplane pilot training for flying a plane by using a flight simulator. There are some general 3D visualization workstations or software packages that let users prepare and visualize some 3D structures. However, none of these are tailored to a laparoscopic ultrasound guided ablation procedure, which may make it hard or even impossible to use for preparing for a laparoscopic ultrasound guided ablation procedure.

SUMMARY OF THE INVENTION

The present disclosure generally relates to systems, methods, devices, and non-transitory computer readable media corresponding to interactive 3D scope and needle placement and measurement techniques for laparoscopic ultrasound guided ablation procedure. In accordance with various embodiments, described in greater detail herein, these procedures may be used in pre-surgical planning and/or during actual surgery for guidance reference. Furthermore, in some embodiments, techniques and technical solutions associated with performing direct interaction schemes in 3D space for placing and adjusting an ultrasound probe and ablation needle may be provided. Additionally, techniques and technical solutions associated with performing direct measurements in 3D space for various surgical related measurements may also be provided.

In one embodiment, a method for determining a placement of an ultrasound transducer for a procedure is described. The method may be implemented by a computing system including at least one processor, memory, and communications circuitry. The method includes, for instance, rendering a first three dimensional ("3D") environment on a display device associated with the computing system. The first 3D environment may include first images of a first body region of a patient and second images including a first virtual representation of an ablation needle placed at a first location within the first body region and a second virtual representation of the ultrasound transducer being placed at a second location with the first body region. A determination may then be made as to whether the first virtual representation and the second virtual representation collide at a first collision point. At least one parameter may be adjusted, where the at least one parameter is associated with at least one of: a first orientation of the second virtual representation and a first position of the second virtual representation. A determination may then be made whether the first virtual representation and the second virtual representation collide in response to the at least one parameter being adjusted. Furthermore, second position data indicating a third location of the second virtual representation after the at least on parameter has been adjusted may be stored if no collision between the first virtual representation and the second virtual representation is determined.

In another embodiment, a system for determining a placement of an ultrasound transducer for a procedure is described. The system, for instance, may include at least one computing device including at least one processor, memory, and communications circuitry. The system includes a patient three-dimensional ("3D") environment generation system configured to render a first 3D environment on a display device associated with the computing system. The first 3D environment may include first images of a first body region of a patient and second images including a first virtual representation of an ablation needle placed at a first location within the first body region and a second virtual representation of the ultrasound transducer being placed at a second location with the first body region. The computing system also includes a visual feedback system configured to determine that the first virtual representation and the second virtual representation collide at a first collision point. The computing system further includes a transducer adjustment system configured to adjust at least one parameter associated with at least one of: a first orientation of the second virtual representation and a first position of the second virtual representation. The visual feedback system may further be configured to determine whether the first virtual representation and the second virtual representation collide in response to the at least one parameter being adjusted, and store second position data indicating a third location of the second virtual representation after the at least on parameter has been adjusted. The second position data may be stored if there is collision between the first virtual representation and the second virtual representation.

Other concepts relate to software for implementing the present teaching on developing a virtual agent. A software product, in accord with this concept, includes at least one machine-readable non-transitory medium and information carried by the medium. The information carried by the medium may be executable program code data, parameters in association with the executable program code, and/or information related to a user, a request, content, or information related to a social group, etc.

In yet another embodiment, machine readable and non-transitory medium having data recorded thereon for determining a placement of an ultrasound transducer for a procedure is described, where the data, when read by the machine, causes the machine to render a first three dimensional ("3D") environment on a display device associated with the computing system. The first 3D environment may include first images of a first body region of a patient and second images including a first virtual representation of an ablation needle placed at a first location within the first body region and a second virtual representation of the ultrasound transducer being placed at a second location with the first body region. The data also causes the machine to determine whether the first virtual representation and the second virtual representation collide at a first collision point. The data also causes the machine to adjust at least one parameter associated with at least one of: a first orientation of the second virtual representation and a first position of the second virtual representation. The data also causes the machine to determine whether the first virtual representation and the second virtual representation collide in response to the at least one parameter being adjusted. The data further causes the machine to store second position data indicating a third location of the second virtual representation after the at least on parameter has been adjusted if there is collision between the first virtual representation and the second virtual representation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

It is noted that this U.S. patent or application file includes at least one drawing executed in color. Copies of this patent or patent application publication with color drawings will be provided by the U.S. patent office upon request and payment of the necessary fees. The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

Figure 1:
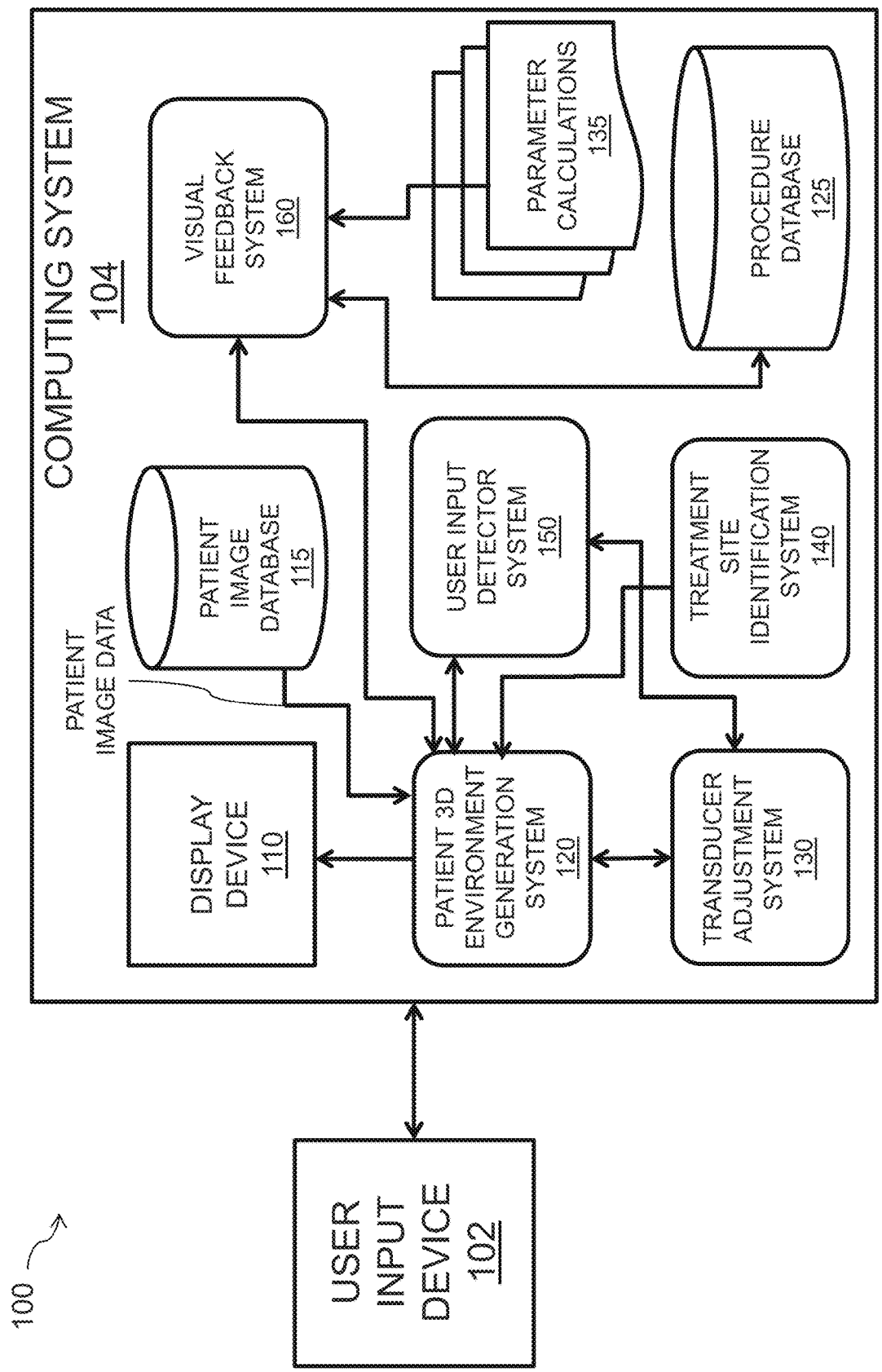
FIG. 1 is an illustrative diagram of a computing environment including an exemplary computing system and an exemplary user input device, in accordance with various embodiments.

The present disclosure generally relates to systems, methods, devices, and non-transitory computer readable media corresponding to interactive 3D scope and needle placement and measurement techniques for laparoscopic ultrasound guided ablation procedure. As described previously, none of the existing general 3D visualization workstations or software packages that allow a user to prepare and visualize certain 3D structures tailored to a laparoscopic ultrasound guided ablation procedure. These issues make it extremely difficult to prepare for such a laparoscopic ultrasound guided ablation procedure.

To overcome the aforementioned inefficiencies and shortcomings, a planning tool designed for a user to interactively place an ultrasound probe and an ablation needle is described, as well as techniques for using such a planning tool to perform operations, and to perform key measurements associated with laparoscopic ultrasound guided ablation procedures. The present teachings describe various embodiments that allow for an optimal location and angle for placing the ultrasound probe to be determined so that an ablation needle can be seen in the field of view of an ultrasound scan image. The present teachings further describe system, methods, devices, and computer readable media that provide physicians with the ability to perform measurements directly in the same 3D space as that which anatomic 3D structures resided in. In this way, users (e.g., surgeons) can obtain and leverage a full picture of the entire, the substantially entire, 3D space, 3D anatomic structures, and any neighboring structures relationships thereto. Visual cues provided by the various embodiments described herein during the planning process gives quick feedback to physicians to allow them make adjustments and reach their intended goals. The simulation results also give physicians references for real surgery. This real-time interaction lets user determine a feasible or desirable setup very quickly, and saves time for surgeons to decide a best or optimal approach for the surgery. The present teachings also provide a clear picture for less experienced practitioners to learn to perform similar surgical procedures using the captured techniques of the more experienced doctors.

In one embodiment, systems, devices, and methods are described corresponding to intelligently aligning two instruments, which may be very hard for users to achieve. The present teaching may allow simulation of the full surgical procedure process—from the moment the ablation needle enters a patient body to the needle reaching the target lesion or area. The present teachings further allow for calculations to be performed corresponding to placing the ultrasound probe so that the ablation needle can be visible within the ultrasound scanning images. The full simulation process may also be recorded and played back for later use and training.

Interactive Operation

In a non-limiting embodiment, a virtual 3D spatial space may be said to already exist (such described by U.S. Pat. No. 7,315,304, the disclosure of which is hereby incorporated herein in its entirety), and that in this virtual 3D spatial space there are meaningful anatomic and/or body structures (e.g., liver, kidney or other organs, ducts/veins/arteries, lesion, rib cages, and/or other boney structures, and skin) that are already segmented from scanned medical data and placed inside the 3D space. For instance, the scanned medical data may correspond to magnetic resonance imaging ("MRI"), computed tomography ("CT"), medical ultrasound, positron emission tomography ("PET"), and/or any other type of imaging technique, or any combination thereof, as persons of ordinary skill in the art will recognize. This virtual 3D scene may, for instance, be displayed on a 2D screen, such as a computer monitor, laptop, tablet computer, smart phone, or any other type of computing device, or any combination thereof. The interaction and/or manipulation happening inside the exemplary virtual 3D space from a user's input with a user interaction device, such as, and without limitation, a computer mouse, keyboard, and/or stylus, may be converted into 3D actions applied to one or more objects located inside the 3D virtual space.

FIG. 1 is an illustrative diagram of a computing environment including an exemplary computing system and an exemplary user input device, in accordance with various embodiments. In a non-limiting embodiment, computing environment 100 may include at least one user input device 102 and at least a first computing system 104. User input device 102, in one embodiment, may correspond to a computer mouse, a keyboard, a stylus, one or more sensors, 3D manipulation gloves, or any other suitable input device, or any combination thereof. Furthermore, user input device 102 may also correspond to a standalone device, such as, but not limited to, a mobile device (e.g., a smart phone, tablet, personal digital assistant, laptop, etc.), or a computing device (e.g., desktop computer, camera, etc.).

Computing system 104, in some embodiments, may include a display device 110, a patient 3D environment generation system 120, a transducer adjustment system 130, a treatment system identification system 140, a user input detector system 150, and a visual feedback system 160. Furthermore, computing system 104 may include a patient image database 115 and a procedure database 125. Patient image database 115 may be configured to store patient image data associated with one or more patients. For example, patient image database 115 may store MRI scans, CT scans, PET scans, or any other suitable type of medical image data, or any combination thereof. Procedure database 125 may be configured to store one or more parameter settings associated with placement and/or orientation of one or more objects for a procedure. For example, procedure database 125 may store an exemplary position and orientation of an ultrasound transducer and/or ablation needle for a LUSA procedure to be performed on a patient. In some embodiments, procedure database 125 may store information associated with a simulation procedure performed by a user to identify a suitable placement and/or orientation of one or more objects for a real-life procedure.

Computing system 104 may further store one or more parameter calculations 135. Parameter calculations 135 may correspond to any suitable model and/or program capable of identifying an angle, a depth, a length, and/or a location, amongst other features, associated with information useful for a user to know for a procedure to be performed. For example, parameter calculations 135 may store information regarding how to calculate a yaw angle of an ultrasound transducer, as well as an approximate location of a xiphoid process within a patient based on one or more characteristics of the patient. More details and description with regard to one or more of the components of computing environment 100 will be described in greater detail herein. Furthermore, persons of ordinary skill in the art will recognize that additional or fewer components may be included within computing system 104, and the aforementioned and foregoing are merely illustrative. For instance, one or more databases may be located external to computing system 104 and capable of being accessed via a network (e.g., the Internet) by computing system 104.

Figure 2:
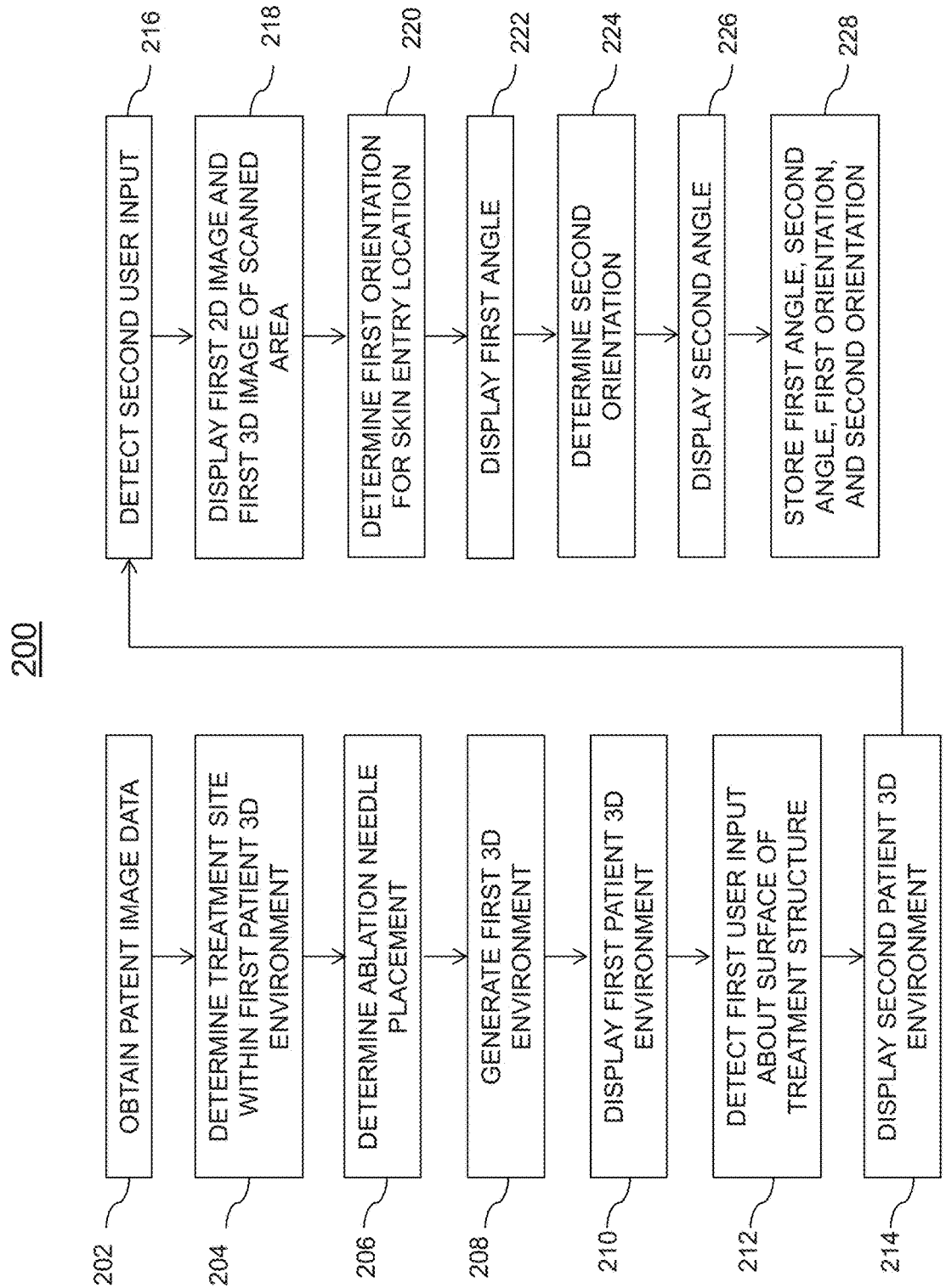
FIG. 2 is an illustrative flowchart of an exemplary process for developing a procedure for determining a placement of an ultrasound transducer, in accordance with various embodiments.

FIG. 2 is an illustrative flowchart of an exemplary process for developing a procedure for determining a placement of an ultrasound transducer, in accordance with various embodiments. Process 200, in one non-limiting embodiment, may begin at step 202. At step 202, patient image data may be obtained. For instance, patient image data may be obtained from patient image database 115. In another scenario, the patient image data may be obtained directly from an image capture device, such as, and without limitation, an MRI machine, a CT machine, and/or a PET machine.

At step 204, a treatment site within a first patient 3D environment may be determined. For instance, the location of a lesion or other item for which medical intervention may be needed may be indicated by the patient image data. In some embodiments, the treatment site may also include a placement/location of a virtual representation of an ultrasound transducer and probe to be adjusted and/or modified based on one or more aspects as described herein. At step 206, a placement of an ablation needle for the procedure may be determined. The ablation needle may be capable of delivery therapy needed for the lesion, and therefore the placement of the needle relative to one or more internal organs may be required. A more detailed description of this aspect may be found below with reference to FIGS. 8A and 8B, for example. The treatment site determination and the ablation needle placement determination may be described below with reference to FIGS. 3A and 3B.

At step 208, a first 3D environment may be generated. For instance, patient 3D environment generation system 120 may generate a first 3D environment representing a region of a patient's body where a procedure is to be performed. In some embodiments, the first 3D environment may include a virtual representation of a treatment site, such as a lesion or tumor to be treated, as well as a virtual representation of a medical object, such as an ablation needle.

At step 210, the first 3D environment may be displayed by display device 110. Display device 110, in one embodiment, may correspond to a display device, such as a touch screen, which may be any size and/or shape and may be located at any portion of computing system 104 and/or be in communication with computing system 104. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Still further, a touch screen may, in some embodiments, correspond to a display device including capacitive sensing panels capable of recognizing touch inputs thereon. For instance, display device 110 may correspond to a projected capacitive touch ("PCT"), screen include one or more row traces and/or driving line traces, as well as one or more column traces and/or sensing lines. In some embodiments, display screen 110 may be an optional component for computing system 104.

At step 212, a first user input about a surface of a treatment structure may be detected. For instance, first patient 3D environment displayed by display device 110 may include a representation of a liver being displayed. In some embodiments, a user may move an input device, such as input device 102, about a surface of the representation to change a view of that representation. For example, by scrolling a mouse over the surface (e.g., virtual surface) of the representation of the liver, a user may be capable of changing a view of that representation to a more optimal view. For instance, a user may scroll about the surface of the liver to determine a better view of a scanning region of an ultrasound transducer placed on the liver, which may be capable of detecting the presence of the ablation needle. A more detailed description of user inputs detected and the actions that those inputs may be related to is described below with reference to FIGS. 4A and 4B.

At step 214, a second patient 3D environment may be displayed. The second patient 3D environment, in one embodiment, may correspond to a view of the representation of the liver, as well as any surrounding virtual anatomic objects, that are now viewable in response to the detected user inputs of step 212. Persons of ordinary skill in the art will recognize that, in some embodiments, steps 212 and 214 may be optional.

At step 216, a second user input may be detected. For instance, an input to user input device 102 may be detected thereby and/or by computing system 104. For example, a user may click a mouse, press a key of a keyboard, or touch a touch screen, associated with user input device 102. At step 218, in response to the second user input, computing system 104 may display a first 2D image and a first 3D image of a scanned area. For instance, the 2D image and the 3D image may be displayed by display device 110. A more detailed description of this may be described below with reference to FIG. 12.

At step 220, a first orientation for a skin entry location may be determined. The skin entry location may correspond to an entry point of a patient with which an ablation needle and/or ultrasound transducer (or any other medical device), may be inserted within a patient. A more detailed description of this may be described below with reference to FIG. 12.

At step 222, a first angle may be displayed by a display device. For example, an angle of the transducer relative to one or more objects or positions may be displayed. At step 224, a second orientation of the transducer may be determined. At step 226, a second angle may be displayed by a display device. For example, a yaw angle and/or a pitch angle of the transducer may be displayed. A more detailed description of steps 220-226 may be described below with reference to FIGS. 12, 14A, and 14B. At step 228, the first angle, second angle, first orientation, and second orientation, may be stored by procedure database 125. In some embodiments, one or more of the first angle, second angle, first orientation, and second orientation need not be stored, and persons of ordinary skill in the art will recognize that the aforementioned is merely exemplary.

Figure 3A:
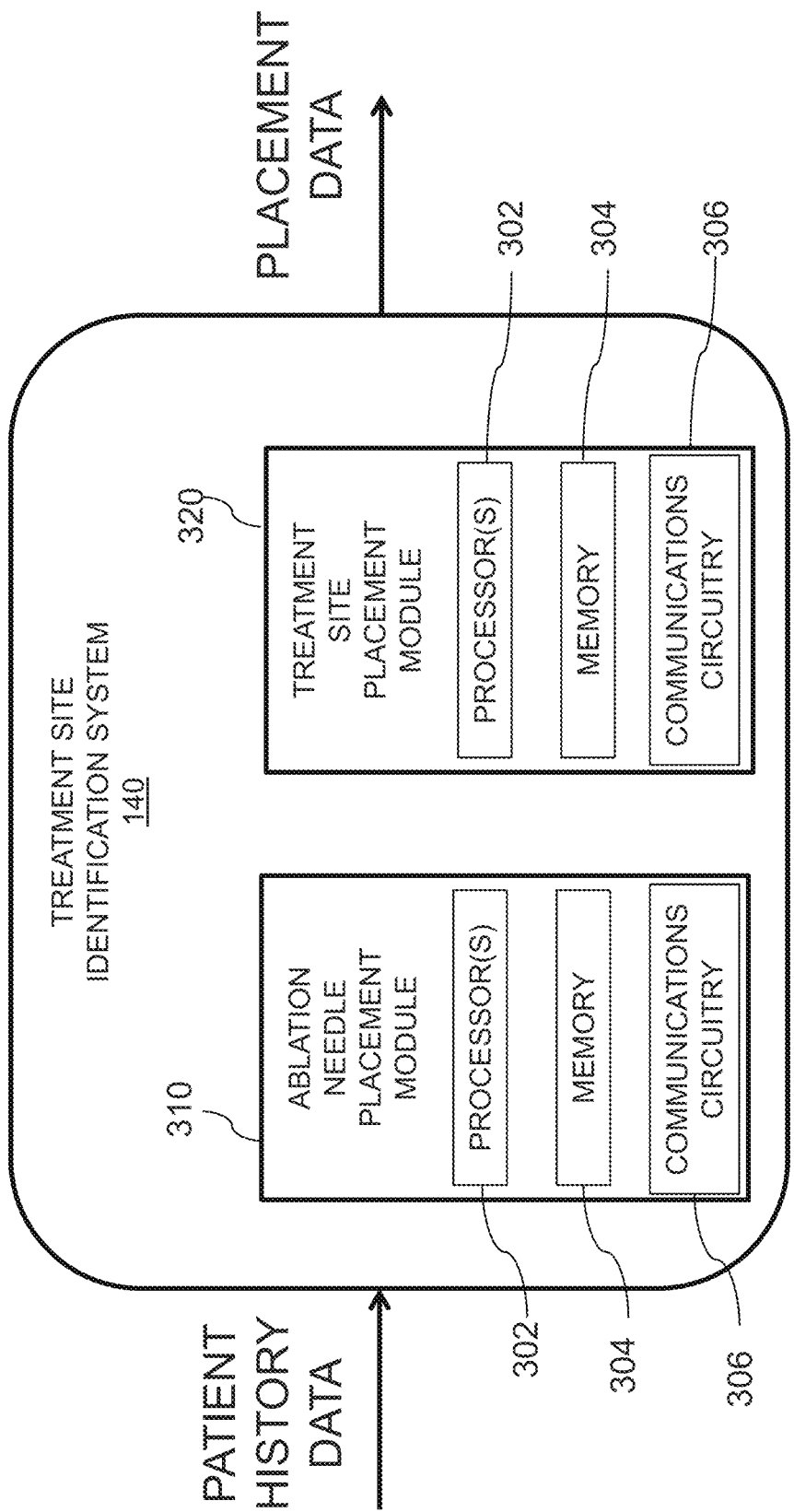
FIG. 3A is an illustrative diagram of an exemplary treatment site identification system, in accordance with various embodiments.

FIG. 3A is an illustrative diagram of an exemplary treatment site identification system, in accordance with various embodiments. FIG. 3A describes an exemplary instance of treatment site identification system 140 of computing system 104 of FIG. 1. In one embodiment, treatment site identification system 140 includes an ablation needle placement module 310 and a treatment site placement module 320. However, persons of ordinary skill in the art will recognize that additional or fewer components/modules may be included, and the aforementioned is merely exemplary. Treatment site identification system 140 may be configured to receive patient history data, such as one or more patient images (e.g., MRIs, CT scans, etc.), and may output placement data indicating a placement and/or orientation of one or more items to be treated (e.g., a lesion, tumor, etc.), and one or more medical devices, such as an ablation needle.

Each of ablation needle placement module 310 and treatment site placement module 320 may include one or more instances of processor 302, memory 304, and communications circuitry 306. Processor(s) 302 may include any suitable processing circuitry capable of controlling operations and functionality of ablation needle placement module 310 and/or treatment site placement module 320, as well as facilitating communications between various components within computing system 104. In some embodiments, processor(s) 302 may include a central processing unit ("CPU"), a graphic processing unit ("GPU"), one or more microprocessors, a digital signal processor, or any other type of processor, or any combination thereof. In some embodiments, the functionality of processor(s) 302 may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 302 may include its own local memory, which may store program systems, program data, and/or one or more operating systems. However, processor(s) 302 may run an operating system ("OS") for treatment site identification system 130, and/or one or more firmware applications, media applications, and/or applications resident thereon. In some embodiments, processor(s) 302 may run a local client script for reading and rendering content received from one or more websites. For example, processor(s) 302 may run a local JavaScript client for rendering HTML or XHTML content.

Memory 304 may include one or more types of storage mediums such as any volatile or non-volatile memory, or any removable or non-removable memory implemented in any suitable manner to store data for computing system 104. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 304 may be implemented as computer-readable storage media ("CRSM"), which may be any available physical media accessible by processor(s) 302 to execute one or more instructions stored within memory 304. In some embodiments, one or more applications may be run by processor(s) 302, and may be stored in memory 304.

Communications circuitry 306 may include any circuitry allowing or enabling one or more components of computing system 104, such as treatment site identification system 140 including ablation needle placement module 310 and treatment site placement module 320, to communicate with one another, and/or with one or more additional devices, servers, and/or systems. For example, communications circuitry 306 may facilitate communications between patient image database 115 and treatment site identification system 140. In some embodiments, communications circuitry 306 may allow treatment site identification system 140, or any other component included thereon or associated therewith, to communicate across a network 230, such as the Internet. For example, network(s) 230 may be accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications. In some embodiments, a web browser using HTTP may be used for communications. Various additional communication protocols may be used to facilitate communications may include, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP.

Figure 3B:
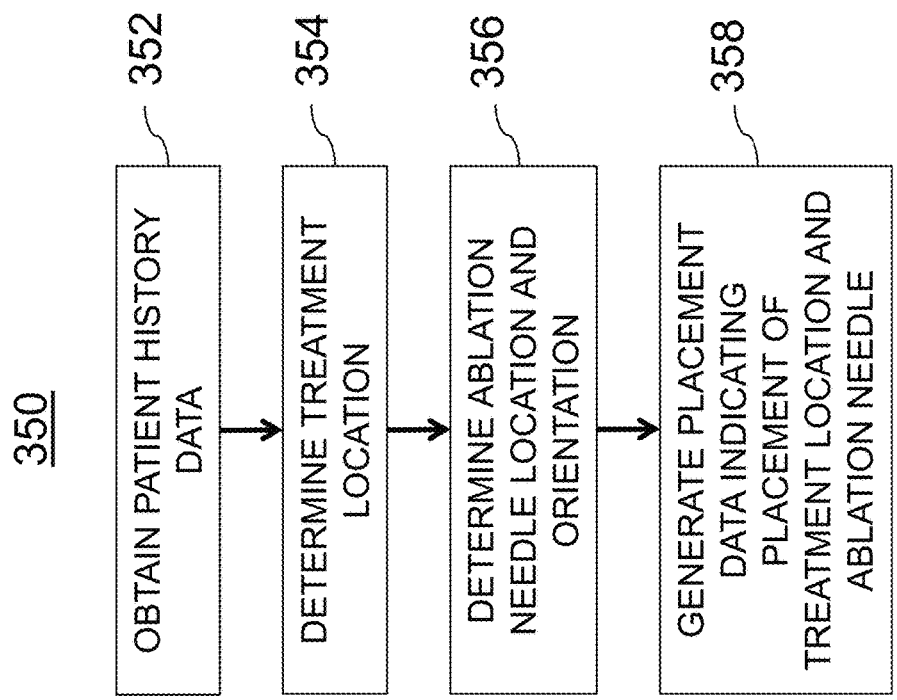
FIG. 3B is an illustrative flowchart of an exemplary process for generating placement data for a patient 3D environment, in accordance with various embodiments.

FIG. 3B is an illustrative flowchart of an exemplary process for generating placement data for a patient 3D environment, in accordance with various embodiments. Process 350 may, in one embodiment, begin at step 352. At step 352, patient history data may be obtained. For instance, patient history data may include patient image data representing one or more scans/images of a region of a patient (e.g., such as an abdomen, head, pelvis, etc.). Furthermore, the patient history data may include information related to a location of one or more items, such as a lesion or tumor, within the region.

At step 354, a treatment location may be determined. For instance, a location of an area or item to be intervened by a medical procedure may be identifiable via the patient history data. Therefore, treatment site placement module 320 may be configured to identify this location within a patient's image data. It should be noted here that the treatment location, in the illustrative embodiment, may correspond to a virtual location within a 3D environment representing a region of a patient where a treatment item is located. At step 356, an ablation needle location and/or orientation may be determined. For instance, ablation need placement module 310 may determine a location of a virtual representation of an ablation needle within the 3D environment. At step 358, placement data indicating a placement of a virtual representation of a treatment location and ablation needle may be generated. In some embodiments, the placement data may be provided to patient 3D environment generation system 120 for use when generating a patient 3D environment.

Figure 4A:
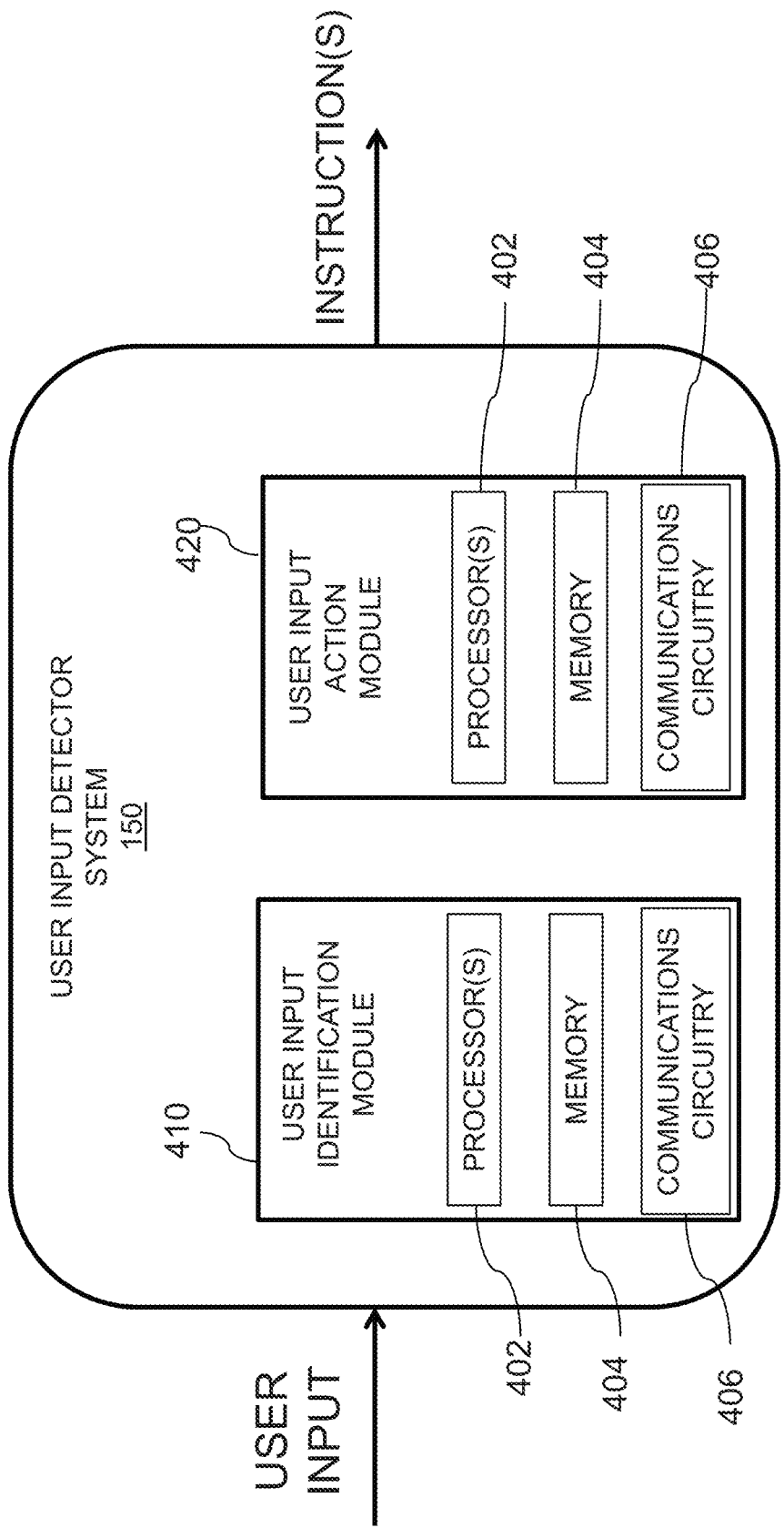
FIG. 4A is an illustrative diagram of an exemplary user input detector system, in accordance with various embodiments.

FIG. 4A is an illustrative diagram of an exemplary user input detector system, in accordance with various embodiments. As seen in FIG. 4A, user input detector system 150 may be described. In a non-limiting embodiment, user input detector system 150 may include a user input identification module 410 and a user input action module 420. However, persons of ordinary skill in the art will recognize that more or fewer modules/components may be included, and the aforementioned is merely exemplary. Further still, each of user input identification module 410 and user input action module 420 may include one or more of processor(s) 402, memory 404, and communications circuitry 406. In some embodiments, processor(s) 402, memory 404, and communications circuitry 406 may be substantially similar to processor(s) 302, memory 304, and communications circuitry 306 of FIG. 3, and the aforementioned is merely exemplary. Furthermore, in some embodiments, user input detector system 150 may be configured to receive one or more user inputs and may generate and send one or more instructions to one or more additional components and/or devices in response to those inputs.

Figure 4B:
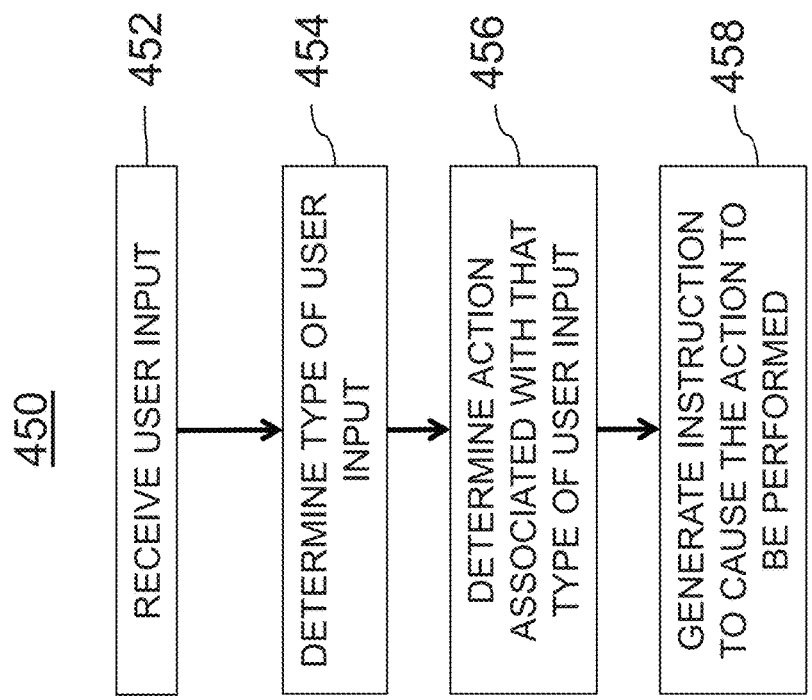
FIG. 4B is an illustrative flowchart of an exemplary process for generating an instruction in response to a user input, in accordance with various embodiments.

FIG. 4B is an illustrative flowchart of an exemplary process for generating an instruction in response to a user input, in accordance with various embodiments. Process 450, in one embodiment, may begin at step 452. At step 452, a user input may be received. In some embodiment, the user input may correspond to an input detected by user input device 102, which may be in communication with computing system 104. For example, a user input may include, but is not limited to, a movement detected by user input device (e.g., a mouse scroll, a mouse movement, a swipe, etc.), an invoking action (e.g., a mouse click, a tap on a touch screen, etc.), and the like.

At step 454, a type of user input may be determined. For instance, user input identification module 410 may be configured to identify a type of input that the user input corresponds to. User input identification module 410, in some embodiments, may include a look up table of different inputs, and the corresponding characteristics that they correspond to. At step 456, an action associated with that type of user input may be determined. For example, a computer mouse movement may correspond to an instruction to cause an orientation of a view of a representation to be modified. As another example, a click of a mouse button may correspond to an instruction to freeze one or more parameters of a process (e.g., lock an angle of a virtual representation of a transducer probe). Persons of ordinary skill in the art will recognize that any suitable type of input may be associated with any suitable action, and the aforementioned are merely illustrative.

At step 458, an instruction to cause the action associated with the identified type of user input to be performed may be generated. The instruction may then be sent by user input detector system 150 to patient 3D generation system and/or transducer adjustment system 130 to cause that action to be performed. For example, if the input indicates that an angle of a transducer is to be adjusted, then an instruction to do so may be sent to transducer adjustment system 130 to configure the adjustments of the transducer, which in turn may be provided to patient 3D environment generation system 120 to generate an updated 3D environment to be rendered by display device 110.

In some embodiments, one type of user input may indicate that a locking or freezing feature is being implemented. In this particular scenario, user input action module 420 may determine that the user input corresponds to a lock feature being enabled. In response, user input detector system 150 may generate an instruction that causes one or more parameters specified by the user input to become non-adjustable. The instruction, in one embodiment, when received by patient 3D environment generation system 120, may cause patient imaging generator 720 to not change that parameter display. For example, if locking feature is implemented such that the ultrasound path (entry point, probe orientation, touch point, transducer orientation) is fixed, and the ablation's target is set, and the system can calculate an optimal path for the ablation needle, including entry point, orientation, and path length. As another example, if the ablation needle path is set, then this parameter may be locked such that the ultrasound path can be calculated. As still yet another example, if the ablation needle path and ultrasound entry point is locked, the ultrasound path can be calculated. Still as another example, the locking feature may allow a plan or a simulation to be saved by procedure database 135 and reloaded later for referencing or training. Simulations can also be made into a video clip or other video playback media.

Figure 5A:
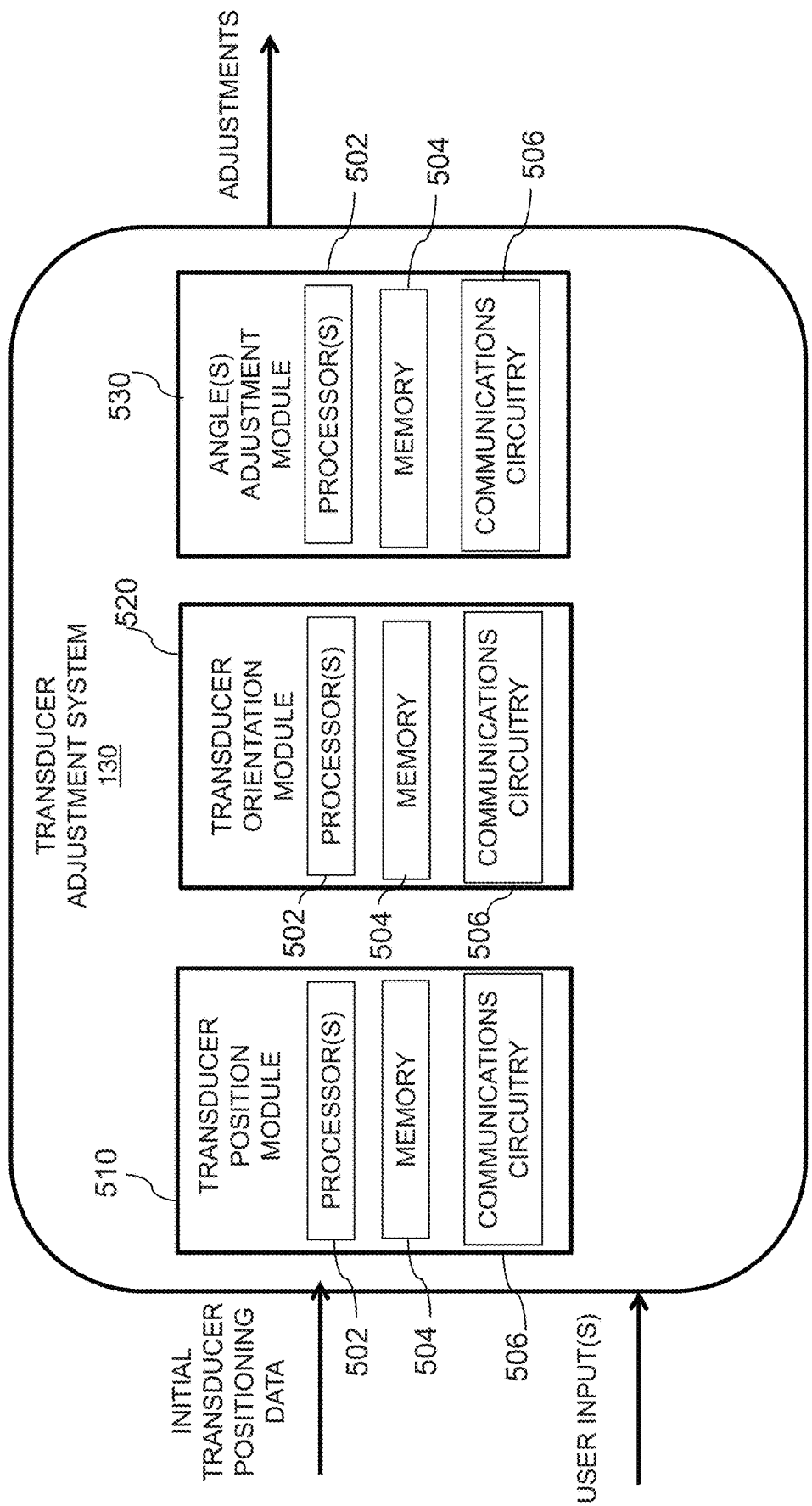
FIG. 5A is an illustrative diagram of an exemplary transducer adjustment system, in accordance with various embodiments.

FIG. 5A is an illustrative diagram of an exemplary transducer adjustment system, in accordance with various embodiments. In a non-limiting embodiment, transducer adjustment system 130 may include a transducer position module 510, a transducer orientation module 520, and an angle(s) adjustment module 530. Persons of ordinary skill in the art will recognize that transducer adjustment system 130 may include one or more additional or fewer components/modules, and the aforementioned are merely exemplary. Furthermore, each of transducer position module 510, transducer orientation module 520, and angle(s) adjustment module 530 may include one or more instances of processor(s) 502, memory 504, and communications circuitry 506. Each of processor(s) 502, memory 504, and communications circuitry 506 may be substantially similar, in one embodiment, to processor(s) 302, memory 304, and communications circuitry 306 of FIG. 3, and the aforementioned is merely exemplary. In some embodiments, transducer adjustment system 130 may be configured to receive initial transducer positing data and/or user inputs, and may output one or more adjustments to be made.

Figure 5B:
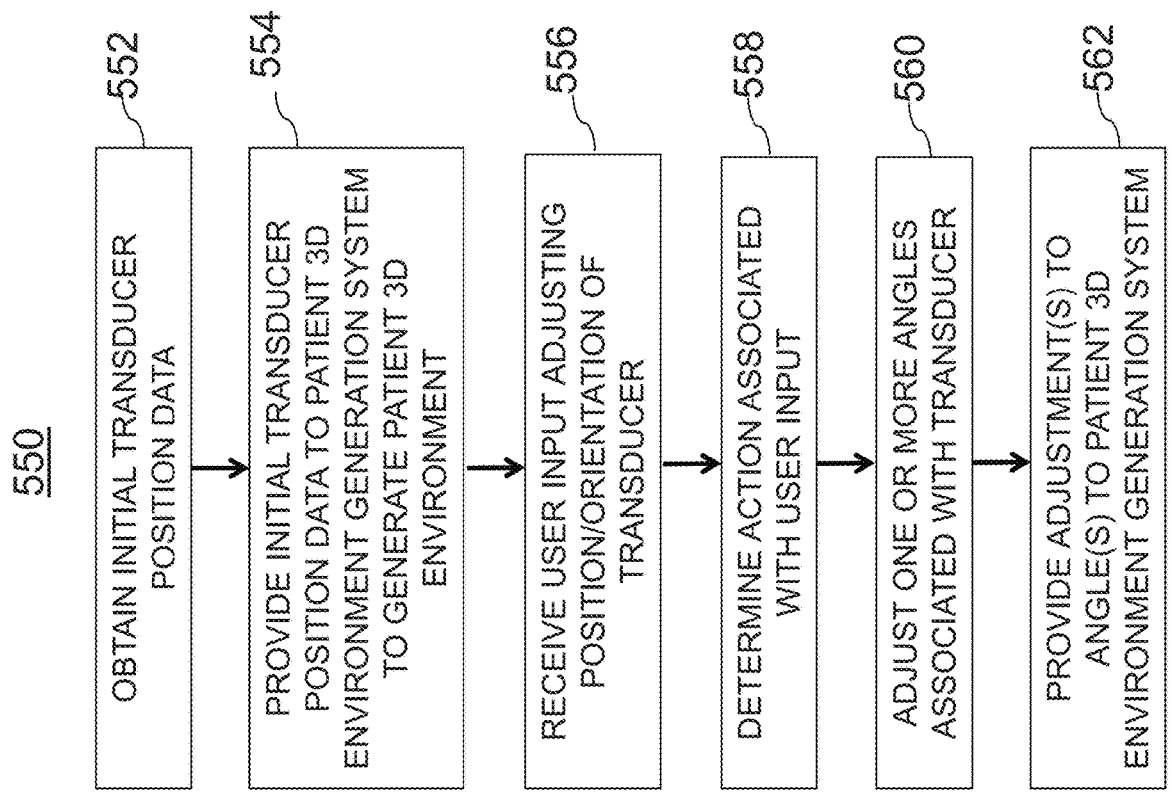
FIG. 5B is an illustrative flowchart of an exemplary process for providing one or more adjustments to a patient 3D environment generation system, in accordance with various embodiments.

FIG. 5B is an illustrative flowchart of an exemplary process for providing one or more adjustments to a patient 3D environment generation system, in accordance with various embodiments. Process 550 may, in one embodiment, begin at step 552. At step 552, initial transducer position data may be obtained. For example, the initial transducer position data may correspond to information indicating a starting position or an initial position associated with a virtual representation of an ultrasound transducer associated with a treatment site for a particular procedure. At step 554, the initial transducer position data may be provided to patient 3D environment generation system 120 to generate a patient 3D environment that includes the virtual representation of the ultrasound transducer.

At step 556, user input adjusting a position/orientation of the ultrasound transducer may be received. In some embodiments, the user input may be received from user input device 102. For example, a user may control a mouse to adjust an angle/position of the transducer. As another example, a user may physically adjust a position/orientation of the virtual representation of the transducer via a virtual reality glove and/or computing system 104. A more detailed explanation of this may be seen below with reference to FIGS. 12 and 14A and 14B.

At step 558, an action associated with the user input may be determined. For instance, if the action is to cause an angle to be adjusted, then this may be determined. At step 560, one or more of the angles associated with the transducer may be adjusted. For instance, a pitch and/or yaw angle of the ultrasound transducer may be adjusted. In some embodiments, angle adjustment module 530 may be configured to identify the action based on the user input and adjust the angle of the transducer accordingly. At step 562, the adjustment(s) to the angle(s) may be provided to patient 3D environment generation system 120.

Figure 6A:
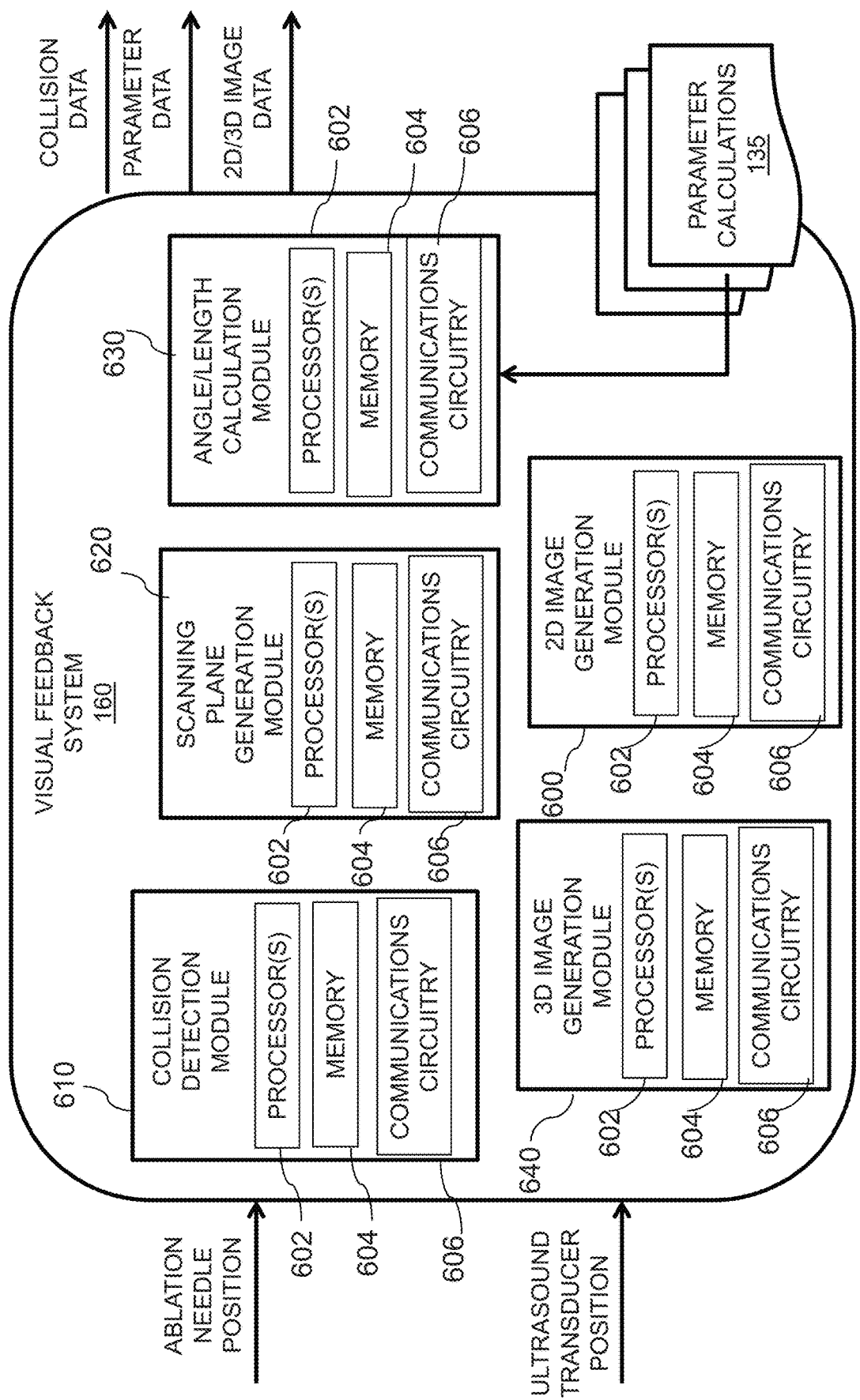
FIG. 6A is an illustrative diagram of an exemplary visual feedback system, in accordance with various embodiments.

FIG. 6A is an illustrative diagram of an exemplary visual feedback system, in accordance with various embodiments. In a non-limiting embodiment, visual feedback system 160 may include a collision detection module 610, a scanning plane generation module 620, an angle/length calculation module 630, a 3D image generation module 640, and a 2D image generation module 600. Each of collision detection module 610, scanning plane generation module 620, angle/length calculation module 630, 3D image generation module 640, and 2D image generation module 600 may include one or more instances of processor(s) 602, memory 604, and communications circuitry 606. Each of processor(s) 602, memory 604, and communications circuitry 606 may be substantially similar, in one embodiment, to processor(s) 302, memory 304, and communications circuitry 306 of FIG. 3, and the aforementioned is merely exemplary. In some embodiments, visual feedback system 160 may be configured to receive one or more of an ablation needle position and/or an ultrasound transducer position, as well as one or more parameter calculations 135, and may output one or more of collision data, parameter data, and/or 2D/3D image data.

Figure 6B:
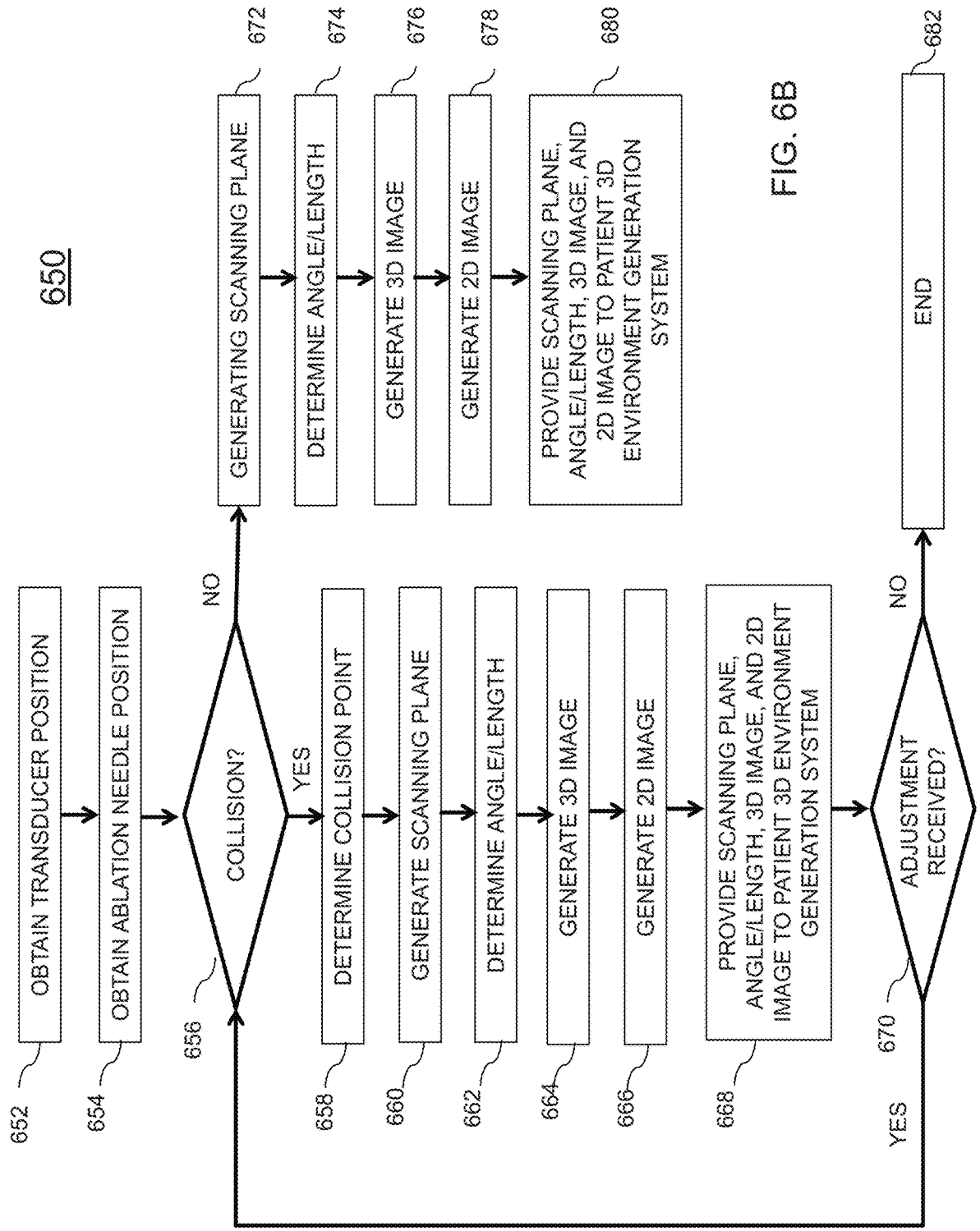
FIG. 6B is an illustrative flowchart of an exemplary process for providing visual feedback to a user, in accordance with various embodiments.

FIG. 6B is an illustrative flowchart of an exemplary process for providing visual feedback to a user, in accordance with various embodiments. Process 650, in a non-limiting embodiment, may begin at step 652. At step 652, a transducer position may be obtained. For instance, initial transducer position data may be obtained, as described in greater detail above. At step 654, an ablation needle position may be obtained. For instance, a position of an ablation needle (or a virtual representation of an ablation needle), for a particular patient treatment may be obtained, as described in greater detail above.

At step 656, a determination may be made as to whether or not there is a collision, or intersection, between the transducer body and the ablation needle. For instance, a collision between these two is described in greater detail below with reference to FIG. 11A. If, at step 656, it is determined that there is a collision, which may be performed by collision detection module 610, then process 650 may proceed to step 658. At step 658, a collision point may be determined. For instance, the collision point may correspond to a 3D representation of where the ablation needle and the ultrasound transducer probe should intersect. At step 660, a scanning plane highlighting the area where the collision is to occur may be generated. In some embodiments, scanning plane generation module 620 may generate the scanning plane indicating the collision. For example, scanning plane 1105-a of FIG. 11A may describe such a scanning plane.

At step 662, an angle/length of the transducer when the collision is occurring may be identified. In some embodiments, angle/length calculation module 630 may determine the angle/length. Furthermore, angle/length calculation module 630 may use one or more parameter calculations 135 (e.g., mathematical modules, geometric identities, anatomical relationships, patient information, etc.) to calculate the angle and/or length of the ultrasound transducer when it is intersecting. At step 664, a 3D image may be generated highlighting the collision. For example, 3D image generation module 640 may generate the 3D image. At step 666, a 2D image may be generated highlighting the collision. A more detailed description of the 3D and 2D images that are generated may be seen below with reference to FIG. 12. At step 668, the scanning plane, angle/length, 3D image, and 2D image may be provided to patient 3D environment generation system 120. This may allow some or all of this information to be displayed to a user such that he/she may see the intersection and the parameters associated with the intersection.

At step 670, a determination may be made as to whether or not an adjustment to an angle/position of the transducer has been received. For example, after identifying the collision, a user may attempt to change a position/angle of the transducer to eliminate the collision. If so, then process 650 may return to step 656 to determine whether or not the collision remains. If not, then process 650 may proceed to step 682 where process 650 may end.

If, at step 656, it is determined that there is no collision, then process 650 may proceed to step 672. At step 672, a scanning plane may be generated. For example, a scanning plane indicating that no collision has occurred may be seen below with reference to FIG. 11B. At step 674, an angle/length may be determined. At step 676, a 3D image may be generated. At step 678, a 2D image may be generated. And at step 680, the scanning plane, angle/length, 3D image, and 2D image may be provided to patient 3D environment generation system 120. In some embodiments, steps 672-680 may be substantially similar to steps 660-668, with the exception that steps 672-680 correspond to a scenario where no collision occurs.

Figure 7A:
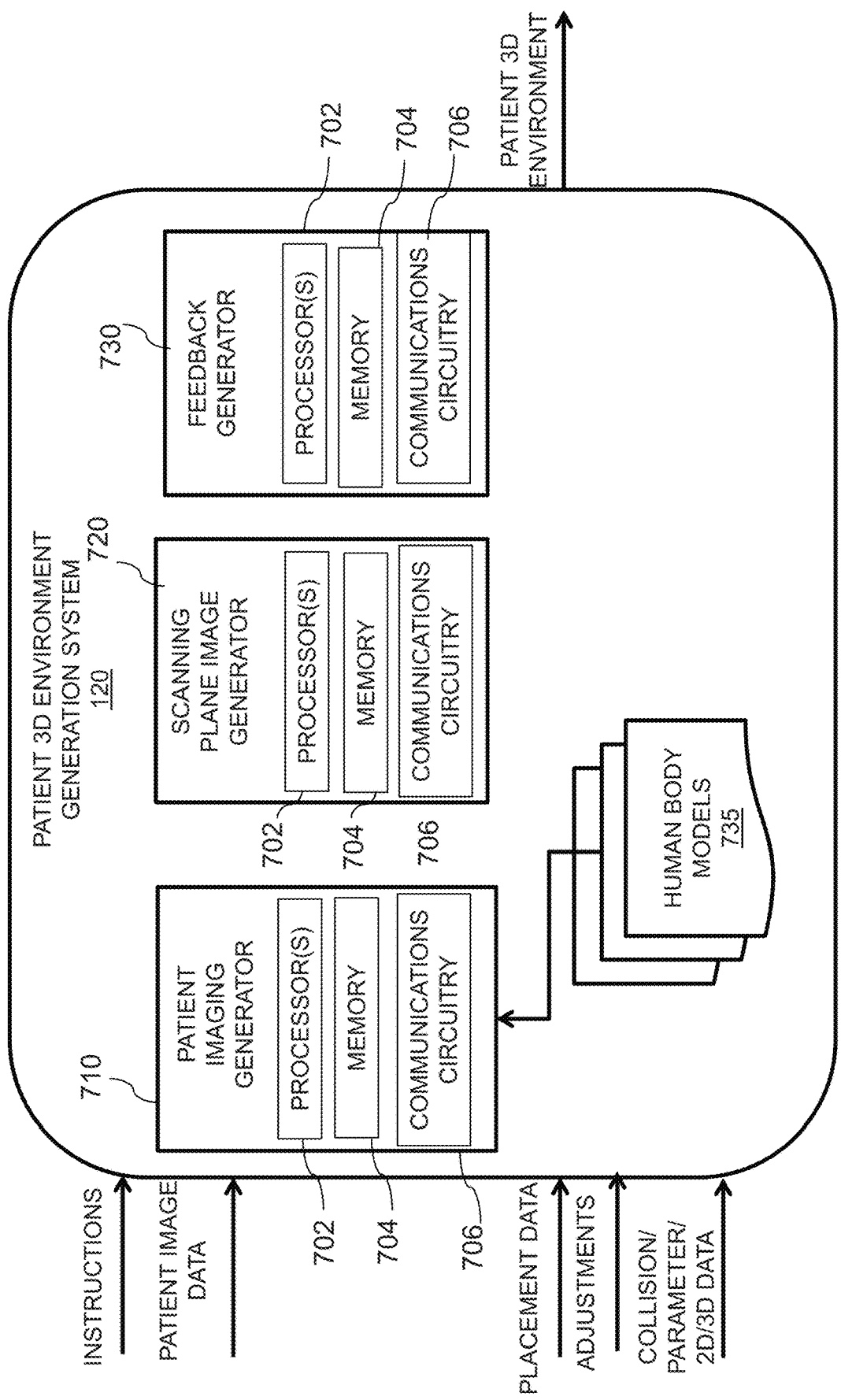
FIG. 7A is an illustrative diagram of an exemplary patient 3D environment generation system, in accordance with various embodiments.

FIG. 7A is an illustrative diagram of an exemplary patient 3D environment generation system, in accordance with various embodiments. Patient 3D environment generation system 120 may include patient imaging generator 720, scanning plane image generator 720, and feedback generator 730. Each of patient imaging generator 720, scanning plane image generator 720, and feedback generator 730 may include one or more instances of processor(s) 702, memory 704, and communications circuitry 706. Each of processor(s) 702, memory 704, and communications circuitry 706 may be substantially similar, in one embodiment, to processor(s) 302, memory 304, and communications circuitry 306 of FIG. 3, and the aforementioned is merely exemplary. In some embodiments, patient imaging generator 710 may be configured to receive/use one or more human body models 735 to generate a 3D environment representing a portion of a human body with which a user may be interested in developing a procedure for. For example, one human body model may correspond to a portion of a human body surrounding a liver to indicate one or more anatomical objects that are commonly found in that region. Patient 3D environment generation system 120 may be configured to receive one or more of instructions, patient image data, placement data, adjustments, and/or collision information, parameter information, and 2D/3D image data. In return, patient 3D environment generation system may be configured to output a patient 3D environment representing a 3D virtual workspace including virtual representations of various anatomical objects (e.g., a liver, surrounding organs/tissue), medical objects (e.g., ablation needles, ultrasound transducers), and/or treatment sites (e.g., lesions, tumors, etc.).

Figure 7B:
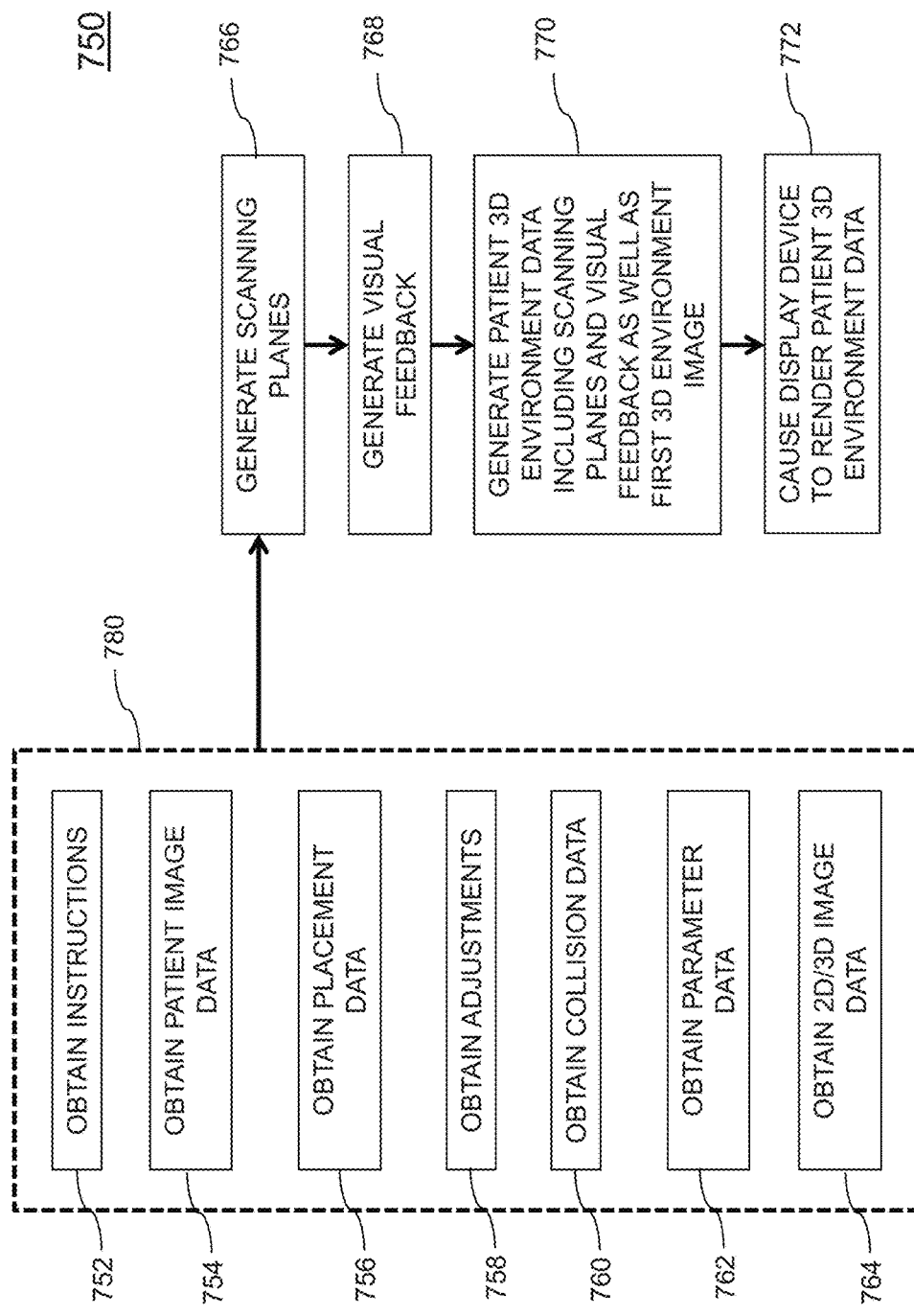
FIG. 7B is an illustrative flowchart of an exemplary process for generating a patient 3D environment, in accordance with various embodiments.

FIG. 7B is an illustrative flowchart of an exemplary process for generating a patient 3D environment, in accordance with various embodiments. Process 750, in a non-limiting embodiment, may begin at step 780. In the illustrative embodiment, step 780 described such that it may include one or more of steps 752-764. Persons of ordinary skill in the art will recognize that any of the steps includes within step 780 may be used to begin process 750. Furthermore, in some embodiments, two or more of the steps included within step 780 may be employed to begin process 750.

In one embodiment, step 780 may include steps 752-764. At step 752, one or more instructions may be obtained. For example, one or more instructions from user input detector system 150 may be obtained. At step 754, patient image data may be obtained. For example patient image data representing one or more scans/images (e.g., MRI scans, CT scans, PET scans, and the like), may be obtained from patient image database 115. At step 756, placement data may be obtained. For example, placement data may be obtained from treatment site identification system 140. At step 758, one or more adjustments may be obtained. For example, adjustments may be obtained from transducer adjustment system 130. At step 760, collision data may be obtained. For example, collision data may indicate a location of a collision identified by collision detection system 610 of visual feedback system 160. At step 762, parameter data may be obtained. For example, parameter data may be obtained from visual feedback system 160. For instance, the parameter data may indicate one or more angles/lengths associated with a transducer probe, which may be calculated by angle/length calculation module 630. At step 764, 2D and/or 3D image data may be obtained. For example the 2D image data and/or the 3D image data may be obtained from visual feedback system 160.

At step 766, one or more scanning planes may be generated. For example, a scanning plane, such as that described below with reference to FIGS. 11A and/or 11B may be generated indicating a collision/no collision. At step 768, visual feedback may be generated. For example, the visual feedback may correspond to an angle associated with one or more of the ultrasound transducer and/or the ablation needle. As another example, the visual feedback may also indicate a length associated with a collision, as well as a position of an insertion site, or any other relevant information.

At step 770, patient 3D environment data including scanning planes and visual feedback, as well as a first 3D environment image may be generated. For example, patient 3D environment generation system 120 may receive various inputs, as described herein, and formulate data representing a 3D patient environment. In some embodiments, the 3D environment with which the patient 3D environment data represents may correspond to an updated version of the 3D environment after one or more adjustments have occurred. At step 772, the patient 3D environment data may be provided to display device 110 such that it may be rendered. For example, display device 110 may display a 3D environment representing a region of interest for a procedure to be performed or being performed.

Figure 8A:
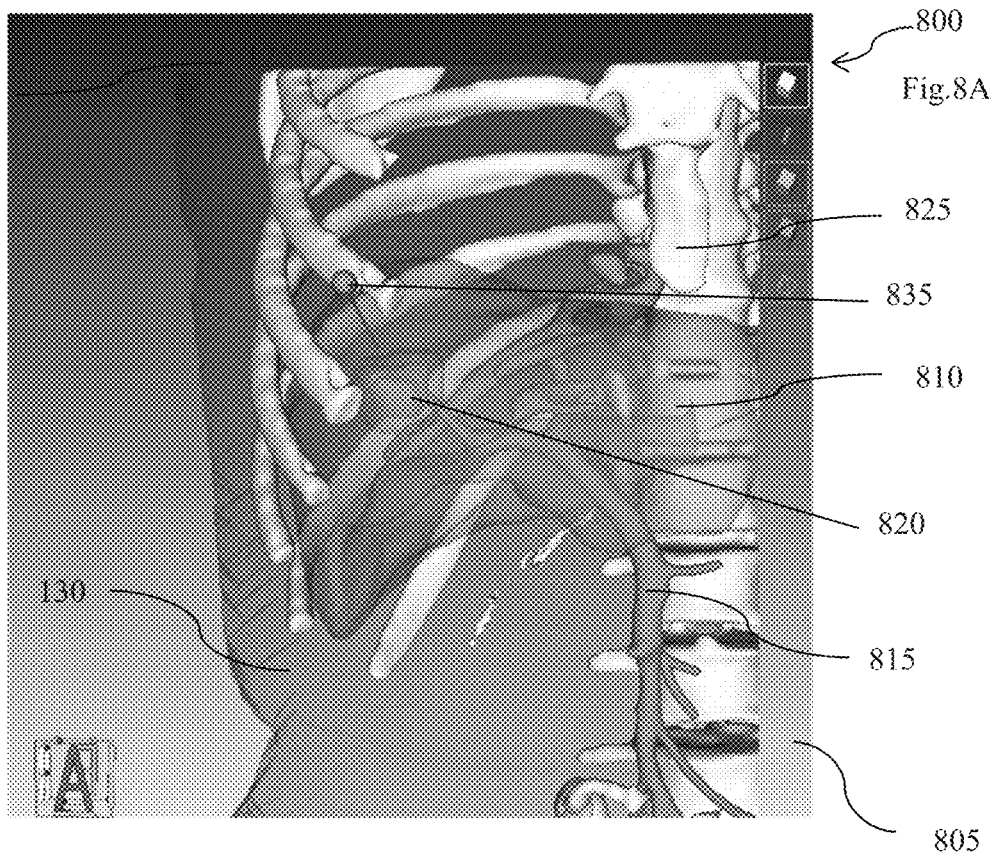
FIGS. 8A and 8B are illustrative diagrams of a front view and a side view of an exemplary virtual environment describing a 3D space, virtual organ, virtual skin, virtual bone, virtual needle, and virtual target (lesion), in accordance with various embodiments.
Figure 8B:
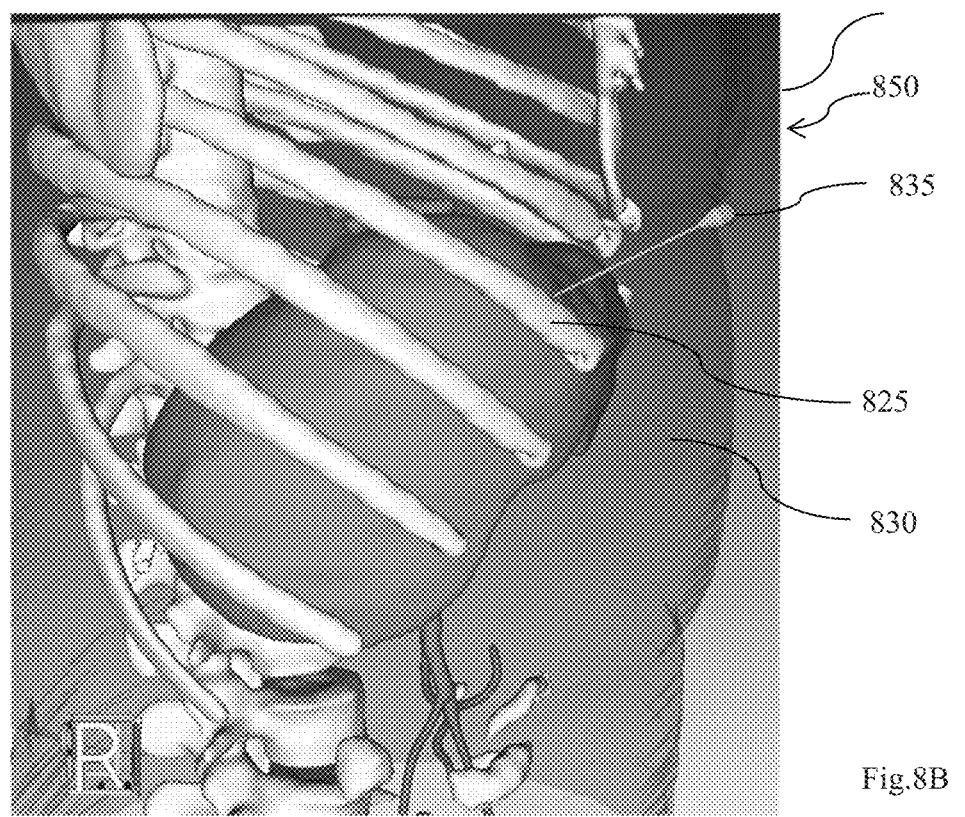

FIGS. 8A and 8B are illustrative diagrams of a front view 800 and a side view 850 of an exemplary virtual environment 805 describing a 3D space, virtual organ, virtual skin, virtual bone, virtual needle, virtual target (lesion), in accordance with various embodiments. Both front view 800 and side view 850 may include virtual 3D environment 805. Some anatomic structures, such as liver 810, artery 815, lesion 820, bone 825, and skin 830 are segmented and displayed in virtual 3D environment 805, as described by FIGS. 8A and 8B.

In a non-limiting embodiment, a virtual representation of an ablation needle 835 may be placed inside virtual 3D environment 805. For instance, ablation needle 835 may be used by a medical professional to target virtual representation of a lesion 810 to be treated. A more detailed description of such targeting procedures may be found in U.S. Patent Application Publication No. 2016/0058521, the disclosure of which is incorporated herein by reference in its entirety. However, persons of ordinary skill in the art will recognize that although ablation needle 835 is described in FIGS. 8A and 8B, any other suitable medical device may be employed and may use the teachings described herein, and the aforementioned is not limited to the use of ablation needles alone.

Figure 9:
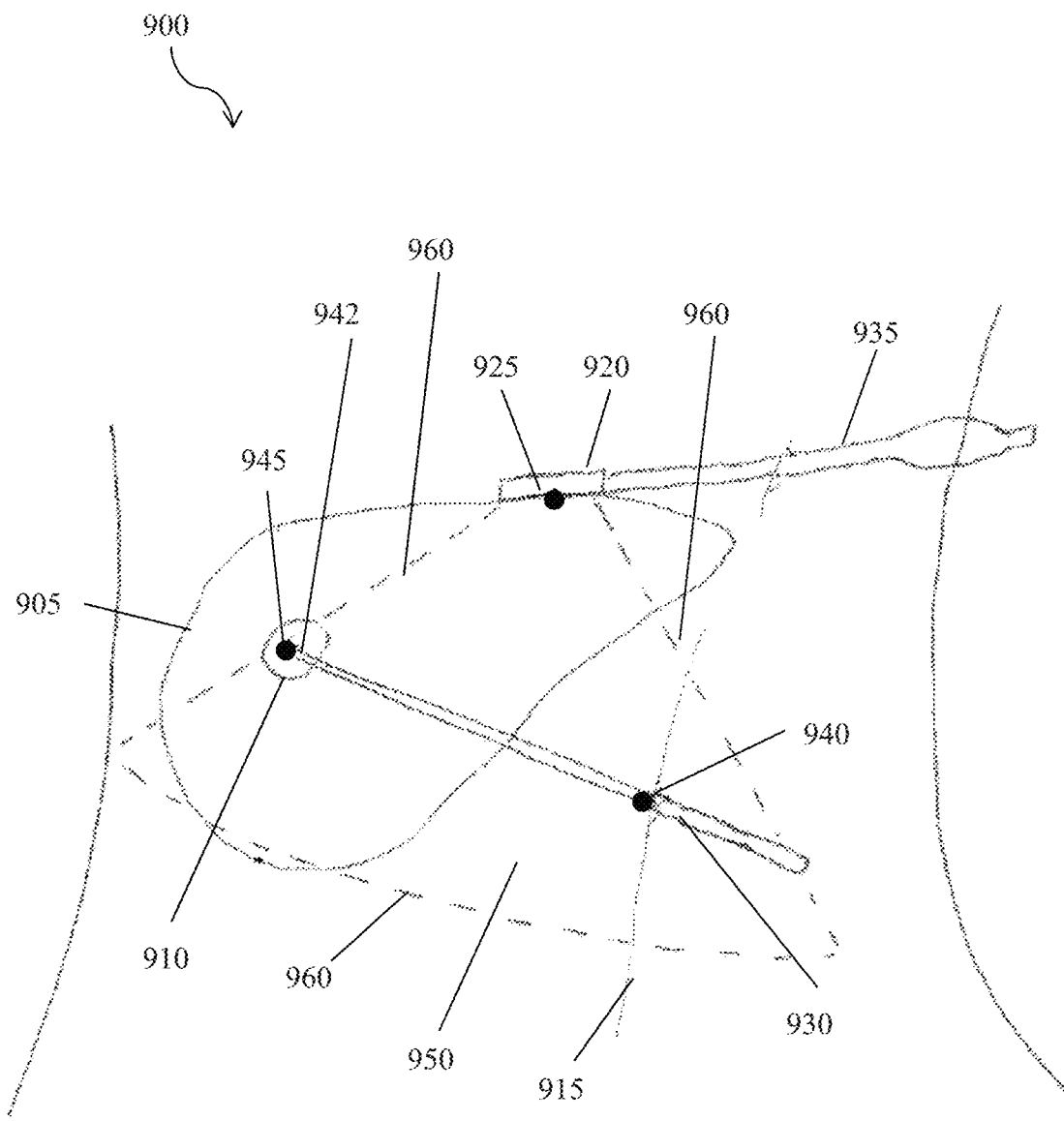
FIG. 9 is an illustrative diagram of a plane geometry representation of an ultrasound transducer and ablation needle, in accordance with various embodiments.

FIG. 9 is an illustrative diagram of a plane geometry representation 900 for an ultrasound transducer and ablation needle, in accordance with various embodiments. In a non-limiting embodiment, during a LUSA procedure, a physician may like to see the ablation needle in an ultrasound scanned image while the physician is advancing, or otherwise moving, the ablation needle towards a target lesion or other structures. In some embodiments, the physician may desire to view the entire ablation needle in the scanned image, while in other embodiments the physician may only need to see a portion of the ablation needle. Even further, a physician may seek to see a portion of the ablation needle during one part of the LUSA procedure, and then at another part of the LUSA procedure, the physician may seek to see the entire ablation needle. Persons of ordinary skill in the art will recognize that although the aforementioned describes a physician performing a LUSA procedure, additional medical procedures may also require a physician or other medical professional to see some or all of a medical device, such as an ablation needle, and the aforementioned is merely exemplary.

As seen in FIG. 9, plane geometry representation 900, in one embodiment, may include a liver 905, a lesion 910 located within liver 905, and body skin 915. A virtual representation of an ablation needle 930 may, in one embodiment, be placed to reach target lesion 910 through body skin 915. Ablation needle 930, for instance, may penetrate through body skin 915 at a point 940 such that a needle tip 942 of ablation needle 930 reaches the target (e.g., target lesion 910) at a point 945. A virtual representation of an ultrasound probe 935, which in one embodiment may include an ultrasound transducer 920 located at an end of ultrasound probe 935, may be placed on a surface of a virtual representation of liver 905. Ultrasound transducer 920 may touch liver 905 at a point 925. Persons of ordinary skill in the art will recognize that although point 925 is illustrated as being singular, this is merely exemplary, as ultrasound transducer 920 may contact liver 905 at an area substantially equal to an area of a surface of a face of ultrasound transducer 920 that is contacting liver 905. Ultrasound transducer 920 may then be configured to scan out an image 950, which may correspond to an expected region capable of being scanned by such an ultrasound transducer 920 in reality, such that, in an illustrative embodiment, scanned image 950 covers a majority (e.g., greater than 50% of) ablation needle 930. For example, ultrasound transducer 920 may obtain an image including content enclosed by dotted lines 960 such that any structures (e.g., some or all of liver 905, needle tip 942, and a portion of ablation needle 930) are visible within scanned image 950. From basic geometry, a plane may be formed by points 940, 945, and 925. In this particular scenario, the plane includes ablation needle 930, however persons of ordinary skill in the art will recognize that, in reality, it may be difficult to adjust an angle of ultrasound transducer 920 so that ultrasound transducer 920 may capture a scan including an entirety (e.g., greater than a threshold value, such as, for example 90%) of ablation needle 930 without certain degrees of experience or external help. Therefore, precise placement of both ablation needle 930 and transducer probe 935 may be required in order to obtain an accurate scan for use by a medical professional.

Figure 10:
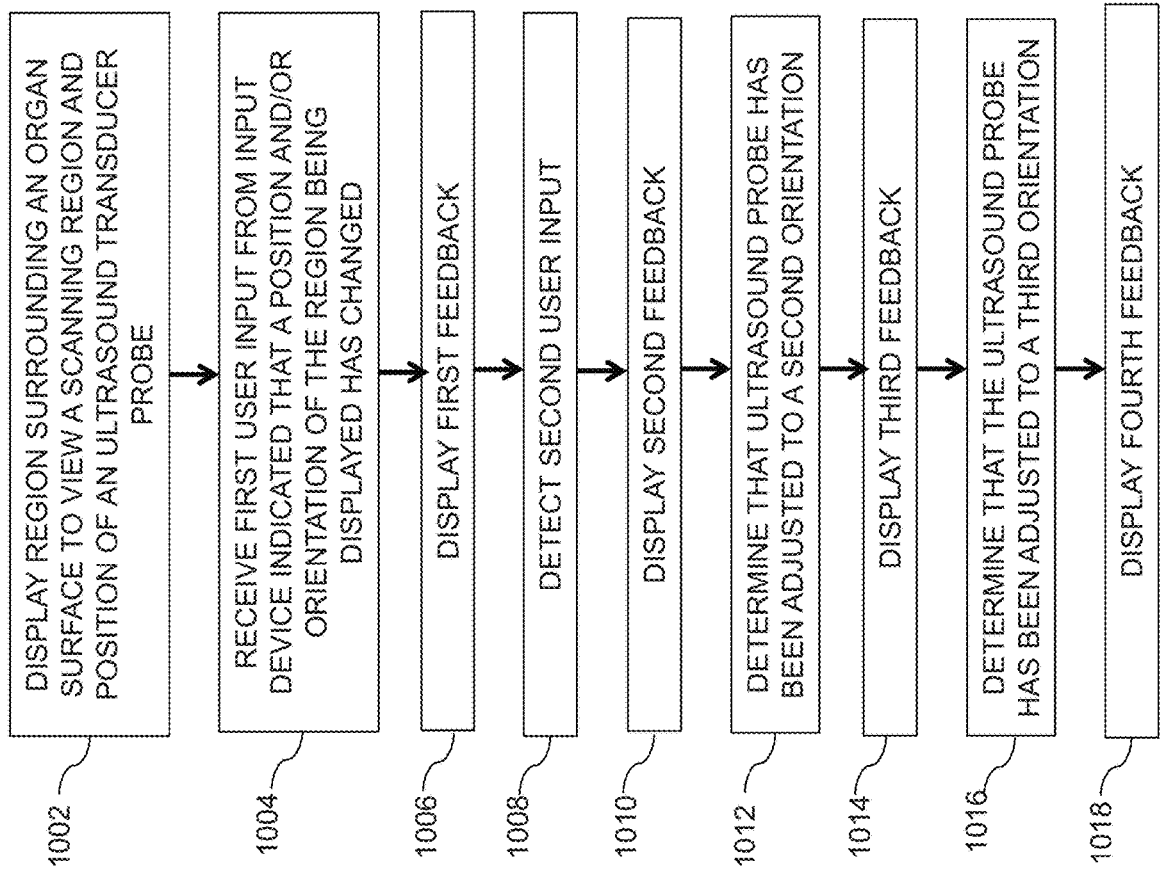
FIG. 10 is an illustrative flowchart of an exemplary process describing placing and adjusting an ultrasound probe, in accordance with various embodiments.

FIG. 10 is an illustrative flowchart of an exemplary processes describing placing and adjusting an ultrasound probe, in accordance with various embodiments. Processes 1000, for instance, may correspond to a workflow for interactively placing an ultrasound probe to a desired orientation and location. In some embodiments, a user, such as a surgeon, may perform some of the steps of process 1000, while a computing system, such as computing system 104 of FIG. 1, may perform other steps, however persons of ordinary skill in the art will recognize that this is merely exemplary.

Process 1000, in a non-limiting embodiment, may begin at step 1002. At step 1002, a 3D environment associated with a patient may be displayed by a display screen associated with a computing system. In some embodiments, the 3D environment may include an organ to be analyzed and/or treated (e.g., a liver). Furthermore, in some embodiments, the 3D environment may include an ablation needle already positioned such that the ablation need is targeting (e.g., interacting) with a particular portion of the organ. For example, the ablation needle may already be positioned within the 3D environment such that a region surrounding an organ surface may be displayed by a display screen associated with a computing device.

At step 1004, a first user input may be received from a user input device indicating that a position and/or orientation of a view of the 3D environment have/has changed. In some embodiments, a user may move an input device, such as a computer mouse, keyboard, stylus, etc., such that a cursor on a corresponding computer screen. By moving the input device (e.g., a mouse), a user may view/observe different graphical scanned regions to pose the probe. This may allow a user to view a scanning region and position of an ultrasound transducer probe from a global perspective for determining an optimal view. The first orientation may be determined such that the ultrasound probe is located on a surface of a structure, such as an organ (e.g., liver), is displayed within the region. For example, after moving the computer mouse, keyboard, stylus, etc., a determination may be made that the input device is placed on top of a major organ's surface. This input device (e.g., mouse cursor) position is somewhat like a shooting ray from a user's point of view to the organ's surface. The cursor position, in one embodiment, may intersect the organ's surface at a point if the cursor is located on top of the surface. This point may, for example, correspond to touching point 925 of ultrasound transducer 920, as described above with reference to FIG. 9.

At step 906, the computing system may display first feedback via the display screen. In some embodiments, at a substantially same time as the first user input is received, the system may be configured to display first feedback to assist in determining a location for the transducer probe. For example, one or more visual cues may be displayed within the displayed image of the region to help the user determine a feasible location to have the ultrasound probe be positioned. The visual cues, as referred to herein, may be described in greater detail below with reference to FIGS. 11A and 11B.

Figures 11A, 11B:
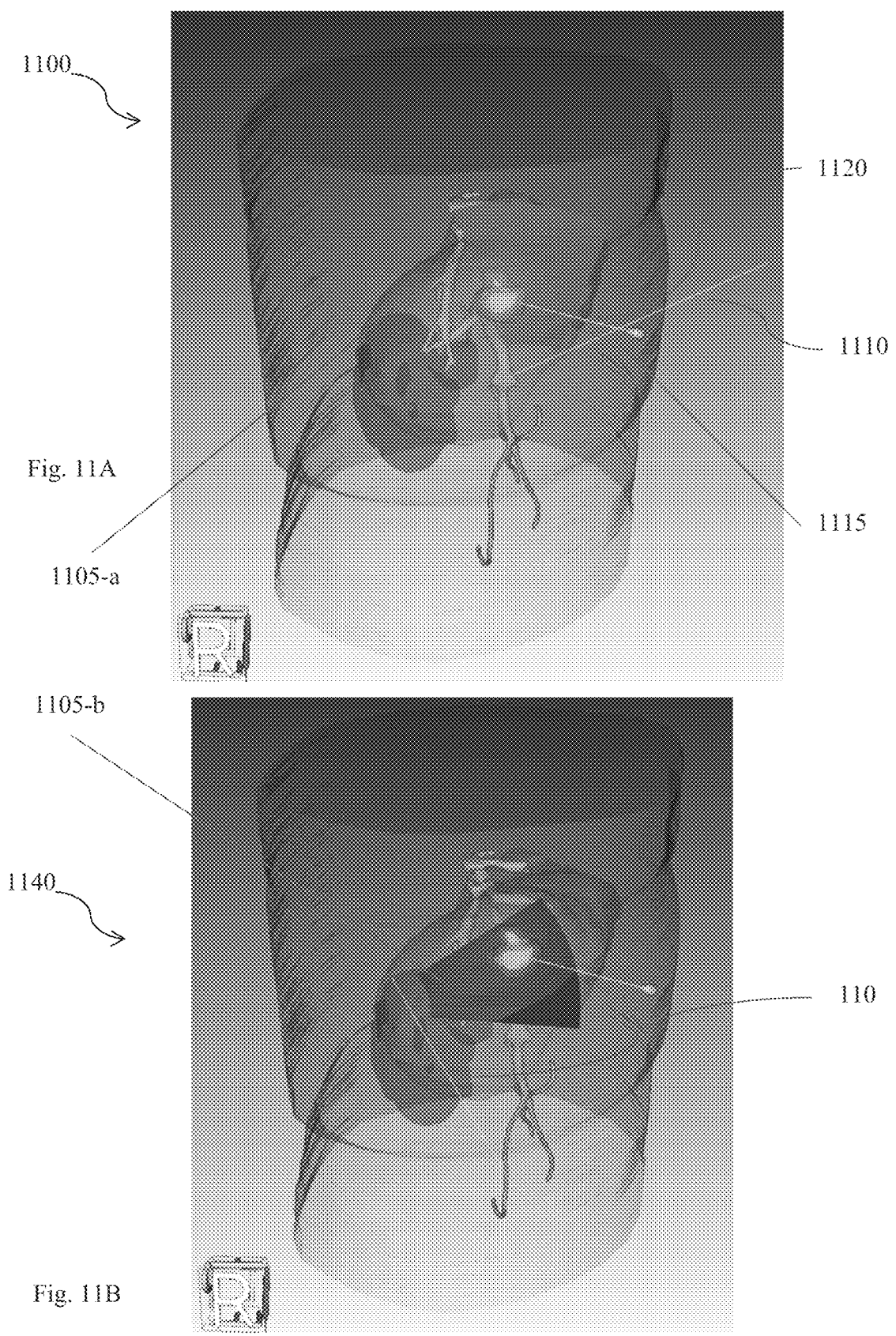
FIGS. 11A and 11B are illustrative diagrams representing manipulations to determine a location and orientation of an ultrasound probe, in accordance with various embodiments.

FIGS. 11A and 11B are illustrative diagrams representing a manipulation to determine a location and orientation of an ultrasound probe, in accordance with various embodiments. The first feedback, as described above with reference to FIG. 10, may correspond to visual feedbacks including, in some embodiments, a scanning planes 1105-*a* and 1105-*b* obtained by an ultrasound transducer of an ultrasound probe stick 1110. Scanning planes 1105-*a* and 1105-*b* may be calculated based on some or all of the principles described previously with reference to FIG. 9 that includes a virtual needle's path and a transducer touching point. As seen from FIG. 11A, a collision 1115 of ultrasound probe stick 110 with an ablation needle 1120 may be identified, and collision 1115 may be indicated with a red plane 1105-*a* within a first image 1100. Second image 1150 of FIG. 1B may depict a scenario where no collision is identified (e.g., no collision or intersection of ultrasound probe stick 1110 with ablation needle 1120). In this particular scenario, the "no-collision" portion may be as represented by blue plane 1105-*b* within second image 1150.

Returning to FIG. 10, at step 1008, a second user input from the input device may be received to lock a position of the transducer probe. In some embodiments, after a desired location on an organ surface is determined, such as at step 1006, the user provides an input via an input device (e.g., clicks a computer mouse's button), which causes that location and orientation of the ultrasound transducer and the scanning plane to "freeze." For example, a user may click on a mouse while the visual cues (e.g., planes 1105-*a* or 1105-*b*) are displayed by a display device, and the position of ultrasound transducer probe stick 1110 and an orientation of ultrasound transducer probe stick 1110 to be identified and stored by the corresponding computing system with which the mouse is associated.

At step 1110, one or more scanned images including the ablation needle may be displayed by the display device. For instance, the computing system may display additional visual information, as shown in greater detail below with reference to FIGS. 12A and 12B. In some embodiments, the computing system may display one or more of a 2D and 3D representation of the scanned area obtained by ultrasound transducer 1120. For example, in the 2D representation, ablation needle 1120 may be visible. In the some embodiments, the computing system may be capable of providing an angle of ultrasound transducer (e.g., ultrasound transducer 920) in relation to a body of the ultrasound probe 935. For example, the angle may represent the angle between the ultrasound transducer and a portion of the ultrasound probe that is located with a body.

Figures 12A, 12B:
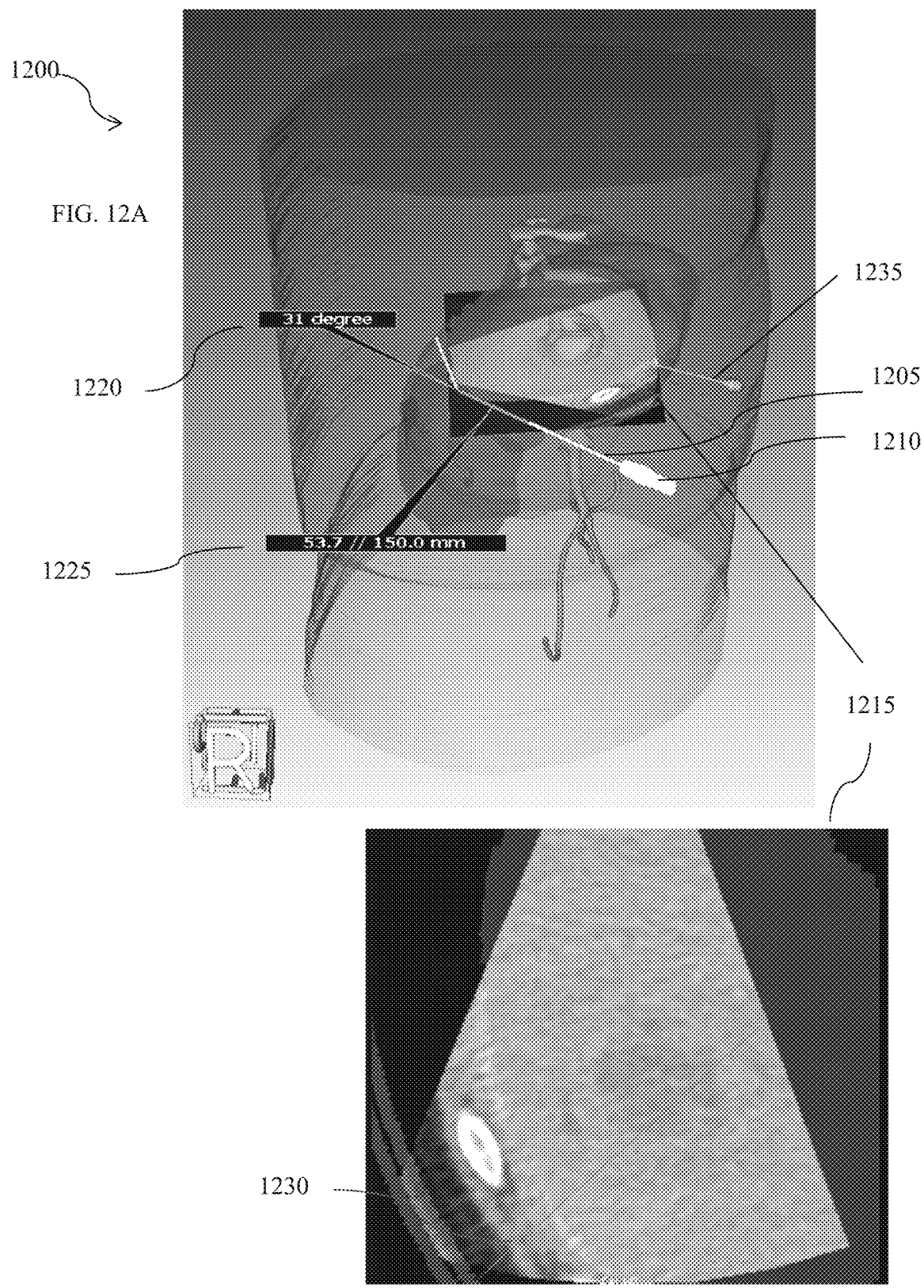
FIGS. 12A and 12B are illustrative diagrams representing manipulations that show supporting visual cues, such as pitch angle popup, in-skin length popup, ultrasound scanning plane, and needle path in an ultrasound plane, in accordance with various embodiments.

FIGS. 12A and 12B are illustrative diagrams representing manipulations that show many supporting visual cues such as pitch angle popup, in-skin length popup, ultrasound scanning plane, and needle path in an ultrasound plane, in accordance with various embodiments. As seen within view 1200 of FIG. 12A, a realistic ultrasound probe 1205 may be displayed with an orientation handle 1210 located at an end of probe 1205. The scanned area may be displayed with a multi-planar rendering ("MPR") image in both 3D view 1200 and 2D view 1215, as seen by FIG. 12B.

Inside 2D MPR image view 1215, a path 1230 of the ablation needle 1235 may be visible. In 3D space, as illustrated by view 1200, a first angle 1220, which may be referred to as a pitch angle, corresponding to an angle between the ultrasound transducer and a body of probe 1205 body may be visible. A second angle 1220, which may be referred to as a pitch angle, in one embodiment, may correspond to an angle that starts at zero degrees as the transducer and a body of probe 1205 are aligned in a straight line before the user adjusts the skin entry point of the ultrasound probe. Additionally displayed may be a length 1225 of the body of probe 1205 inside a patient and a full length of probe 1205, where the length may correspond to a length from the skin entry point to a point that transducer attach to the probe body is located. From these measurements and graphical representation, physicians may obtain a clear idea where to place the ultrasound transducer, what is the pitch angle to adjust from probe control, and/or where to enter the body of the patient.

At step 1012, a determination that the ultrasound probe has been adjusted to a second orientation may occur. In some embodiments, a user may adjust the orientation of the ultrasound probe by grabbing handle 1010 of probe 1205 (as seen in FIG. 12A) in the 3D space and moving probe 1205 accordingly. A more detailed description of the techniques capable of being used to adjust the orientation of the ultrasound probe may be described in U.S. Patent Application Publication No. 2009/0142740, the disclosure of which is hereby incorporated herein by reference in its entirety. During adjustment, a user may see a pose of the probe relative to other objects in the 3D space and may easily determine a desired orientation for probe 1205.

At step 1014, third visual feedback associated with the second orientation may be displayed. In some embodiments, the system may display visual feedback such as an angle associated with the transducer. For instance, pitch angle value 1220 may be updated simultaneously as probe 1205 is being adjusted. This can let the user know whether the orientation is possible or not due to one or more operating limitations of ultrasound probe 1205. Additionally, the possibilities of collision or penetration of probe 1205 through the ribs or other anatomical parts, which should be avoided, may be detected. The detection may be represented by a warning color (such as red) in a body of probe 1205 body to flag the user's attention to the potential collision or penetration.

Figure 13:
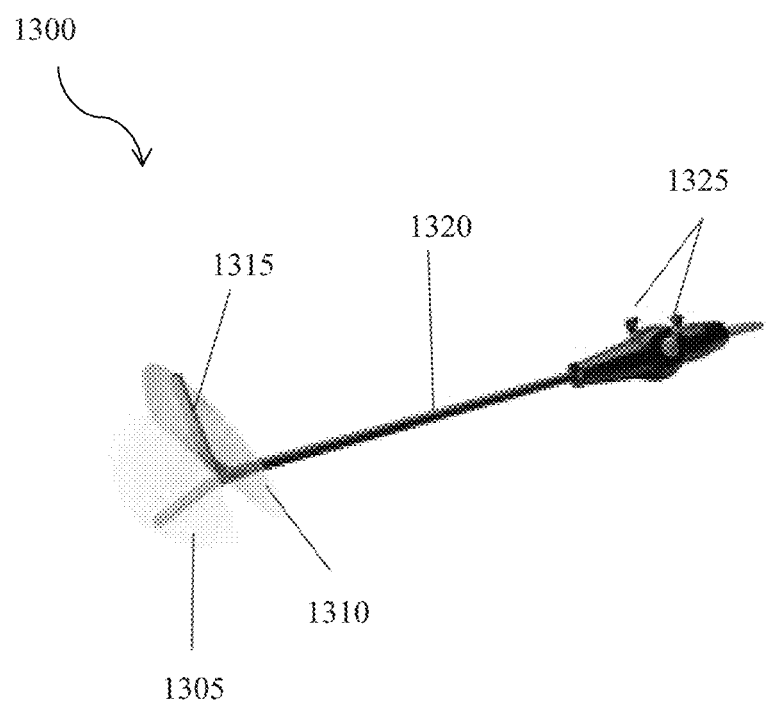
FIG. 13 is an illustrative diagram of an exemplary laparoscopic ultrasound probe indicating a pitch angle and a yaw angle of a transducer with probe body, in accordance with various embodiments.

FIG. 13 is an illustrative diagram of an exemplary laparoscopic ultrasound probe indicating a pitch angle and a yaw angle of a transducer with probe body, in accordance with various embodiments. A laparoscopic ultrasound probe 1300, in some embodiments, may include three main components: a transducer 1315, a probe body 1320, and one or more controls 1325. Transducer 1315 may be adjusted through controls 1325 to change two (or more) angles with respect to probe body 1320. One of these angles may correspond to a pitch angle 1305, while another of these angles may correspond to a yaw angle 1310.

At step 1016, a determination that the ultrasound probe has been adjusted to a third orientation may occur. For instance, a user may adjust a yaw angle 1310 of transducer 1315 with respect to probe body 1320 by grabbing an end of transducer 1315 and moving the end around in a limited half circle range as allowed by a specification of ultrasound probe 1300. This operation may allow a user who just wants to track a tip of an ablation needle tip and does not care much about the ablation needle's length. This may allow the user to obtain one or more scanned images including the ablation needle tip only, for example. Correspondingly, at step 1018, fourth visual feedback associated with the third orientation may be displayed. For instance, the computing system may be configured to display yaw angle 1310.

Figure 14A:
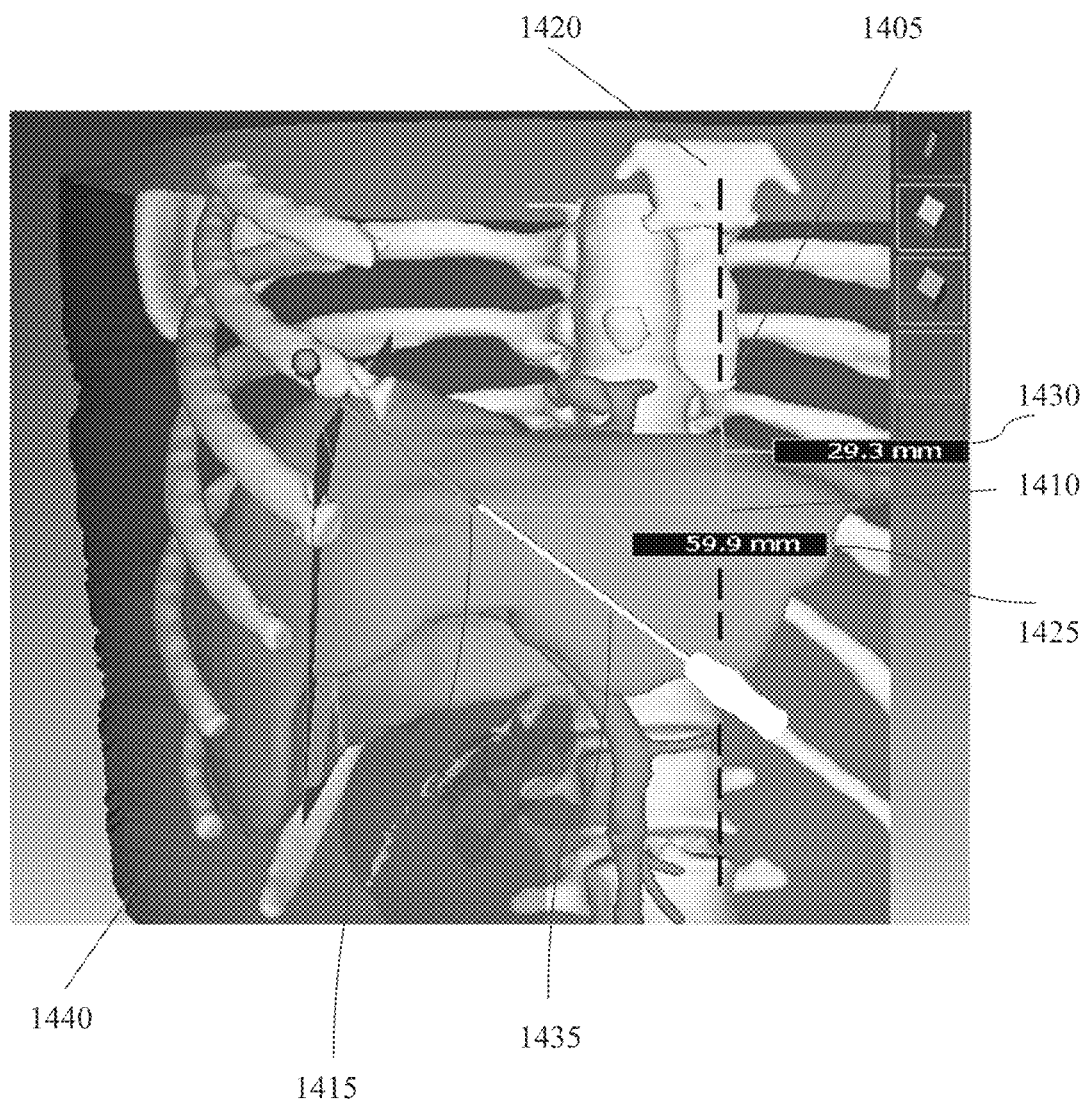
FIGS. 14A and 14B are illustrative diagrams of an exemplary representation describing on skin measurements to help physicians locate an ultrasound probe insertion point and orientation, in accordance with various embodiments.
Figure 14B:
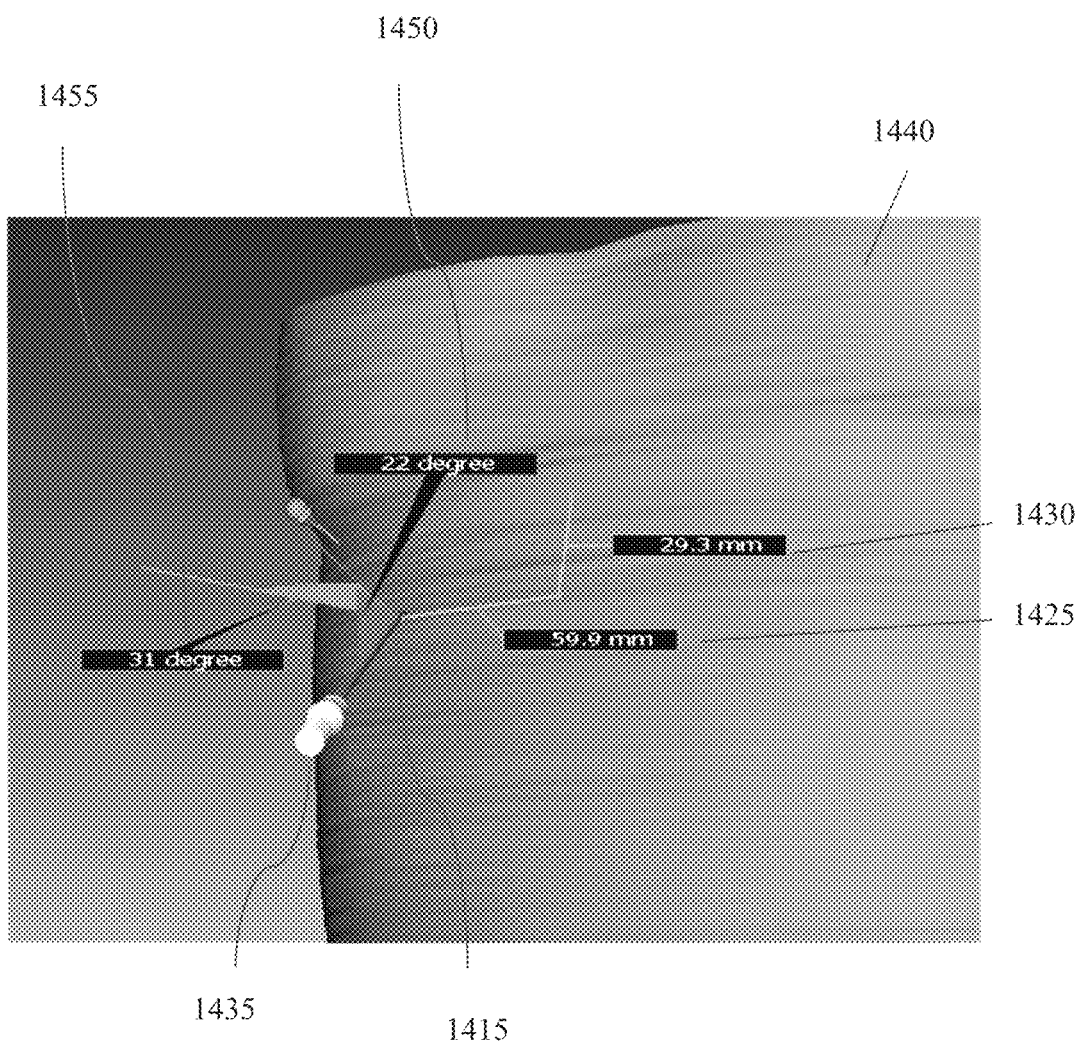

FIGS. 14A and 14B are illustrative diagrams of an exemplary representation describing on-skin measurements to help physicians locate an ultrasound probe's insertion point and orientation, in accordance with various embodiments. After an ultrasound probe's location is decided, physicians may want to pinpoint exactly where the entry point is on the body of a patient. In some embodiments, one technique to determine the entry point may be to perform two distance measurements.

As depicted in FIG. 14A, with skin 1440 shown as being transparent, a first distance that may be measured may correspond to a distance from a skin entry point 1410 of an ultrasound probe 1435 to a point 1415 on a vertical line 1420, where vertical line 1420 represents an exemplary line extending from a patient's head to toes in a middle of body. A second distance that may be measured may correspond to a distance from point 1415 to an anatomic structure, such as, and without limitation, a xiphoid process 1405 along vertical line 1420. Physicians can use these two distances to locate the skin entry point of laparoscopic ultrasound probe 1435 to be used during the actual surgical procedure. These two distances, in some embodiments, may also be provided with the user pointing out the location of xiphoid process 1405 of the patient. After determining the location of xiphoid process 1405, vertical line 1420 of the patient may be determined based, at least partially, on volume data orientation information associated with the patient. Next, a planned probe skin entry point 1410 may be projected to vertical line 1420 to determine a location of point 1415. Distance 1425 from xiphoid process point 1405 to point 1415 can be calculated either in straight distance or along the skin. Distance 1430, corresponding to skin entry point 1410 to point 1415, can also be calculated in straight line or as a curve along the skin, in accordance with various embodiments.

Physicians may also like to know how to insert ultrasound probe 1435 into the patient so that the planned location may be reached. Two angle measurements may provide the inserting orientation information. In FIG. 14B, with skin 1440 being shown as opaque, a first angle 1450 may be measured such that an angle between ultrasound probe 1435 and a projection of probe 1435 on an axial plane through skin entry point 1410 may be determined. A second angle 1455 may be measured such that an angle between the projection line with a vertical line perpendicular to the surgical table that the patient lays may be determined.

Laparoscopic ultrasound controls that can be interactively set and adjusted by users with (a) a set of control parameters on the transducer and (b) a set of control parameters on the entry point of the ultrasound.

Lock Function

One advantage of the present teachings is that users can carry out different simulation scenarios by locking different variables in the simulation. This may give users a fresh new look of an approach for different simulation sessions. The system and method can 'lock' an alignment of the two instruments, namely the ablation needle and the laparoscopic ultrasound probe, per a user's preference or settings. Some examples of user preferences include locking the showing of needle tip on the ultrasound image, and/or locking the showing of needle path on the ultrasound image.

Below, some exemplary embodiments of "lock" are illustrated:

1. If the ultrasound path (entry point, probe orientation, touch point, transducer orientation) is fixed, ablation target is set, and therefore the system can calculate an optimal path for the ablation needle, including entry point, orientation, and path length.
2. If the ablation needle path is set, the ultrasound path can be calculated.
3. If the ablation needle path is set and ultrasound entry point is set, the ultrasound path can be calculated.
4. When a user is interactively adjusting the needle path, corresponding ultrasound settings can be automatically updated to ensure that the ultrasound image(s) shows the needle, and/or the needle tip, as the user prefers.
5. When a user is interactively adjusting the ultrasound probe, a corresponding needle path can also be automatically updated.

Finally, a plan or a simulation can be saved and reloaded later for referencing or training. Simulations can also be made into a video clip or other video playback media.

In some embodiments, the locking feature may be implemented in response to a user input detected by user input device 102. For example, in response to detecting a user input associated with a locking feature, one or more parameters may be stored by procedure database 125. In this way, when an adjustment is made, as described in greater detail above, a locked parameter may not change.

Surgical Simulation

During a real laparoscopic ultrasound guided ablation surgery, after the laparoscopic ultrasound probe is placed inside the patient's body, users typically still need to adjust the ultrasound probe, including adjusting the orientation of the probe at a fixed entry point, transducer touch point and its scanning orientation, etc., on-the-fly to cope with body movements, anatomical structure deformations, and the like. For example, the pressure inside the abdominal air chamber and the degrees of anesthesia may cause different degrees of expansion of abdominal wall. Also the applied pressure of ultrasound probe may cause organ to move or deform. To help users deal with such challenges, the system can simulate a real laparoscopic ultrasound guided ablation surgery procedure by applying a deformation model to mimic the aforementioned abdominal air chamber pressure situation. The corresponding alignment of laparoscopic ultrasound and ablation needle due to deformation can be derived by incorporating deformation information. The various embodiments of the invention may be implemented by software, but may also be implemented in hardware, or in a combination of hardware and software. The invention may also be embodied as computer readable code on a computer readable medium. The computer readable medium may be any data storage device that may thereafter be read by a computer system.

Figure 15:
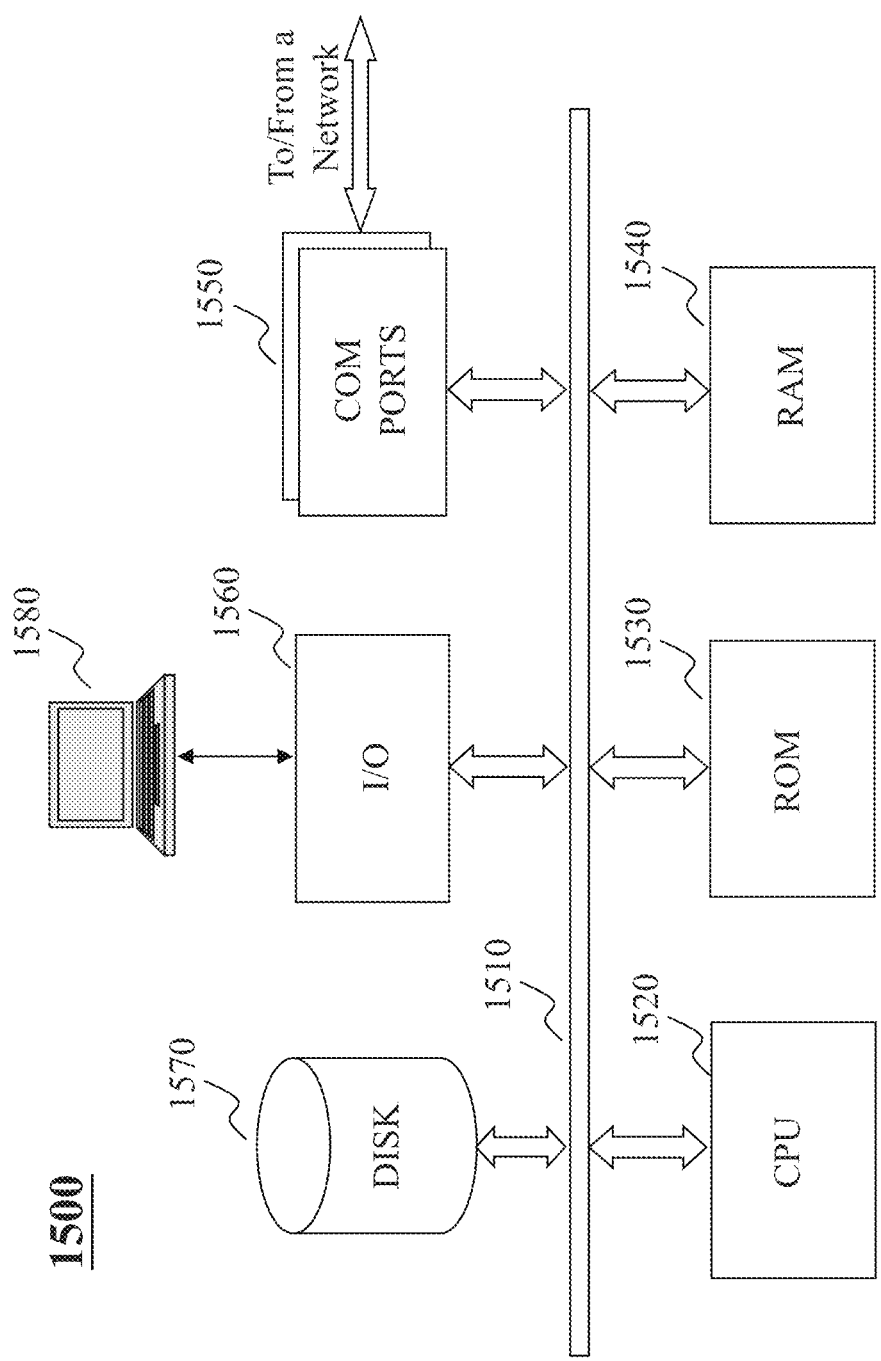
FIG. 15 is an illustrative diagram of exemplary computing system architecture of a computer which can be used to implement the present teaching, in accordance with various embodiments.

FIG. 15 is an illustrative diagram of exemplary computing system architecture of a computer which can be used to implement the present teaching, in accordance with various embodiments. The present teachings include a functional block diagram illustration of a hardware platform which includes user interface elements. A computer 1500, as described herein, may be a general purpose computer or a special purpose computer. Both can be used to implement a specialized system for the present teaching. This computer 1500 may be used to implement any component of the present teachings, as described herein. Although only one such computer is shown, for convenience, the computer functions relating to the present teachings as described herein may be implemented in a distributed fashion on a number of similar platforms, to distribute the processing load.

Computer 1500, for example, includes COM ports 1550 connected to and from a network connected thereto to facilitate data communications. Computer 1500 also includes a central processing unit (CPU) 1520, in the form of one or more processors, for executing program instructions. The exemplary computer platform includes an internal communication bus 1510, program storage and data storage of different forms, e.g., disk 1570, read only memory (ROM) 1530, or random access memory (RAM) 1540, for various data files to be processed and/or communicated by the computer, as well as possibly program instructions to be executed by the CPU. Computer 1500 also includes an I/O component 1560, supporting input/output flows between the computer and other components therein such as user interface element. Computer 1500 may also receive programming and data via network communications.

Hence, aspects of the methods of the present teachings, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a search engine operator or other enhanced ad server into the hardware platform(s) of a computing environment or other system implementing a computing environment or similar functionalities in connection with the present teachings. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the present teachings as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method for determining a placement of an ultrasound transducer for a procedure, the method being implemented by a computing system comprising at least one processor, memory, and communications circuitry, the method comprising:

rendering, by the at least one processor, a first three dimensional ("3D") environment on a display device associated with the computing system, the first 3D environment comprising first images of a first body region of a patient and second images comprising a first representation of a virtual ablation needle placed at a first location within the first body region and a second representation of a virtual ultrasound transducer being placed at a second location within the first body region;

determining, by the at least one processor, whether the virtual ablation needle and the virtual ultrasound transducer, each of which is rendered in the first 3D environment, collide at a first collision point;

adjusting, in response to a collision occurring at the first collision point, at least one parameter associated with at least one of: a first orientation of the virtual ultrasound transducer and a first position of the virtual ultrasound transducer;
determining whether the virtual ablation needle and the virtual ultrasound transducer collide in response to the at least one parameter being adjusted; and
storing, by the at least one processor, position data indicating a third location of the virtual ultrasound transducer after the at least one parameter has been adjusted, the position data being stored by the memory in response to determining an absence of a collision between the virtual ablation needle and the virtual ultrasound transducer.

2. The method of claim 1, further comprising:
obtaining, by the at least one processor, and prior to the first 3D environment being rendered by the display device, first patient imaging data representing the first images, the first patient imaging data being obtained from the memory;
obtaining, by the at least one processor, first patient treatment data representing the second images, the first patent treatment data being obtained from the memory; and
generating, by the at least one processor, first 3D environment data representing the first 3D environment.

3. The method of claim 2, further comprising:
providing the first 3D environment data to the display device such that the first 3D environment is rendered by the display device.

4. The method of claim 1, wherein adjusting the at least one parameter further comprises:
adjusting at least one of: a yaw angle and a pitch angle associated with the second representation of the virtual ultrasound transducer.

5. The method of claim 1, further comprising:
generating, by the at least one processor, and prior to the at least one parameter being adjusted, first scanning plane data representing a first scanning plane indicating a collision area associated with the first collision point, the first scanning plane being of a first color and first shape; and
rendering the first scanning plane on the display device in addition to the first 3D environment.

6. The method of claim 1, further comprising:
determining, by the at least one processor, that a first user input has been detected via a first input device, the first user input causing a view of the first 3D environment to be adjusted.

7. The method of claim 1, further comprising:
determining, by the at least one processor, that a first user input has been detected via a first input device;
determining an action associated with the first user input;
determining that the action is associated with causing at least a first parameter of the at least one parameter to be locked such that the first parameter is unable to be adjusted.

8. The method of claim 1, further comprising:
determining, by the at least one processor, at least one value associated with the at least one parameter;
generating display data representing the at least one value; and
rendering the display data on the display device.

9. The method of claim 1, further comprising:
determining that a first user input has been detected by a first user input device;
generating, in response to an action associated with the first user input being determined, at least a two dimension ("2D") image associated with a portion of the first 3D environment, the 2D image comprising at least a portion of the first virtual representation; and
render the at least 2D image on the display device at a substantially same time as the first 3D environment.

10. A system for determining a placement of an ultrasound transducer for a procedure, the system comprising at least one computing device comprising at least one processor, memory, and communications circuitry, the system comprising:
a patient three-dimensional ("3D") environment generation system configured to render a first three dimensional ("3D") environment on a display device associated with the computing system, the first 3D environment comprising first images of a first body region of a patient and second images comprising a first representation of a virtual ablation needle placed at a first location within the first body region and a second representation of a virtual ultrasound transducer being placed at a second location within the first body region;
a visual feedback system configured to determine whether the virtual ablation needle and the virtual ultrasound transducer, each of which is rendered in the first 3D environment, collide at a first collision point; and
a transducer adjustment system configured to adjust, in response to a collision occurring at the first collision point, at least one parameter associated with at least one of: a first orientation of the virtual ultrasound transducer and a first position of the virtual ultrasound transducer, wherein the visual feedback system is further configured to:
determine whether the virtual ablation needle and the virtual ultrasound transducer collide in response to the at least one parameter being adjusted; and
store position data indicating a third location of the virtual ultrasound transducer after the at least one parameter has been adjusted, the position data being stored by the memory in response to determining an absence of a collision between the virtual ablation needle and the virtual ultrasound transducer.

11. The system of claim 10, further comprising:
a treatment site identification system configured to:
obtain first patient imaging data representing the first images, the first patient imaging data being obtained from the memory; and
obtain first patient treatment data representing the second images, the first patent treatment data being obtained from the memory, wherein the patient 3D environment generation system is further configured to generate first 3D environment data representing the first 3D environment.

12. The system of claim 11, wherein the patient 3D environment generation system is further configured to:
provide the first 3D environment data to the display device such that the first 3D environment is rendered by the display device.

13. The system of claim 10, wherein adjustment of the at least one parameter further comprises the transducer adjustment system to be configured to:
adjust at least one of: a yaw angle and a pitch angle associated with the second representation of the virtual ultrasound transducer.

14. The system of claim 10, wherein the visual feedback system is further configured to:
generate first scanning plane data representing a first scanning plane indicating a collision area associated with the first collision point, the first scanning plane being of a first color and first shape, such that the
patient 3D environment generation system is further
configured to:
  render the first scanning plane on the display device in
    addition to the first 3D environment.
15. The system of claim 10, further comprising:
a user input detector system configured to determine that
  a first user input has been detected via a first input
  device, the first user input causing a view of the first 3D
  environment to be adjusted.
16. The system of claim 10, further comprising:
a user input detector system configured to:
  determine, by the at least one processor, that a first user
    input has been detected via a first input device;
  determine an action associated with the first user input;
  determine that the action is associated with causing at
    least a first parameter of the at least one parameter to
    be locked such that the first parameter is unable to be
    adjusted.
17. The system of claim 10, wherein the transducer
adjustment system is further configured to:
  determine at least one value associated with the at least
    one parameter, the patient 3D environment system is
    further configured to:
  generate display data representing the at least one value;
    and
  render the display data on the display device.
18. The system of claim 10, further comprising:
a user input detector system configured to determine that
  a first user input has been detected by a first user input
  device, wherein the visual feedback system is further
  configured to:
  generate, in response to an action associated with the
    first user input being determined, at least a two
    dimension ("2D") image associated with a portion of
    the first 3D environment, the 2D image comprising
    at least a portion of the first virtual representation.
19. The system of claim 18, wherein the patient 3D
environment generation system is further configured to:
  render the at least 2D image on the display device at a
    substantially same time as the first 3D environment.
20. A machine readable and non-transitory medium having data recorded thereon for determining a placement of an ultrasound transducer for a procedure, wherein the data, when read by the machine, causes the machine to:
  render a first three dimensional ("3D") environment on a
    display device associated with the computing system,
    the first 3D environment comprising first images of a
    first body region of a patient and second images comprising a first representation of a virtual ablation needle
    placed at a first location within the first body region and
    a second representation of a virtual ultrasound transducer being placed at a second location within the first
    body region;
  determine whether the virtual ablation needle and the
    virtual ultrasound transducer, each of which is rendered
    in the first 3D environment, collide at a first collision
    point;
  adjust, in response to a collision occurring at the first
    collision point, at least one parameter associated with at
    least one of: a first orientation of the virtual ultrasound
    transducer and a first position of the virtual ultrasound
    transducer;
  determine whether the virtual ablation needle and the
    virtual ultrasound transducer collide in response to the
    at least one parameter being adjusted; and
  store position data indicating a third location of the virtual
    ultrasound transducer after the at least one parameter
    has been adjusted, the position data being stored by the
    memory in response to determining an absence of a
    collision between the virtual ablation needle and the
    virtual ultrasound transducer.
21. The medium of claim 20, wherein the data, when read
by the machine, further causes the machine to:
  obtain, prior to the first 3D environment being rendered
    on the display device, first patient imaging data representing the first images, the first patient imaging data
    being obtained from the memory;
  obtain first patient treatment data representing the second
    images, the first patent treatment data being obtained
    from the memory; and
  generate first 3D environment data representing the first
    3D environment.
22. The medium of claim 21, wherein the data, when read
by the machine, further causes the machine to:
  provide the first 3D environment data to the display
    device such that the first 3D environment is rendered on
    the display device.
23. The medium of claim 20, wherein the at least one
parameter being adjusted further comprises the data, when
read by the machine, to:
  adjust at least one of: a yaw angle and a pitch angle
    associated with the second representation of the virtual
    ultrasound transducer.
24. The medium of claim 20, wherein the data, when read
by the machine, further causes the machine to:
  generate, prior to the at least one parameter being
    adjusted, first scanning plane data representing a first
    scanning plane indicating a collision area associated
    with the first collision point, the first scanning plane
    being of a first color and first shape; and
  render the first scanning plane on the display device in
    addition to the first 3D environment.
25. The medium of claim 20, wherein the data, when read
by the machine, further causes the machine to:
  determine that a first user input has been detected via a
    first input device, the first user input causing a view of
    the first 3D environment to be adjusted.
26. The medium of claim 20, wherein the data, when read
by the machine, further causes the machine to:
  determine that a first user input has been detected via a
    first input device;
  determine an action associated with the first user input;
    and
  determine that the action is associated with causing at
    least a first parameter of the at least one parameter to be
    locked such that the first parameter is unable to be
    adjusted.
27. The medium of claim 20, wherein the data, when read
by the machine, further causes the machine to:
  determine at least one value associated with the at least
    one parameter;
  generate display data representing the at least one value;
    and
  render the display data on the display device.
28. The medium of claim 20, wherein the data, when read
by the machine, further causes the machine to:
  determine that a first user input has been detected by a first
    user input device;
  generate, in response to an action associated with the first
    user input being determined, at least a two dimension
    ("2D") image associated with a portion of the first 3D environment, the 2D image comprising at least a portion of the first virtual representation; and render the at least 2D image on the display device at a substantially same time as the first 3D environment.

29. The method of claim 1, further comprising:

adjusting, in response to the collision occurring at the first collision point, a pitch angle associated with the second representation of the virtual ultrasound transducer.

* * * * *